(12) United States Patent
Ebenstein et al.

(10) Patent No.: US 12,385,161 B2
(45) Date of Patent: Aug. 12, 2025

(54) MULTI-SAMPLE ARRAY CHIP FOR DNA MODIFICATION QUANTIFICATION

(71) Applicant: Ramot at Tel-Aviv University Ltd., Tel-Aviv (IL)

(72) Inventors: Yuval Ebenstein, Tel-Aviv (IL); Shahar Zirkin, Tel-Aviv (IL); Sapir Margalit, Tel-Aviv (IL); Yael Michaeli Hoch, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1283 days.

(21) Appl. No.: 16/972,691

(22) PCT Filed: Jun. 6, 2019

(86) PCT No.: PCT/IL2019/050656
§ 371 (c)(1),
(2) Date: Dec. 7, 2020

(87) PCT Pub. No.: WO2019/234753
PCT Pub. Date: Dec. 12, 2019

(65) Prior Publication Data
US 2021/0254167 A1     Aug. 19, 2021

Related U.S. Application Data

(60) Provisional application No. 62/681,186, filed on Jun. 6, 2018.

(51) Int. Cl.
*C40B 30/04*     (2006.01)
(52) U.S. Cl.
CPC .................................. *C40B 30/04* (2013.01)
(58) Field of Classification Search
None
See application file for complete search history.

(56) References Cited

U.S. PATENT DOCUMENTS

| | | |
|---|---|---|
| 2003/0170689 A1 | 9/2003 | Stamatoyannapoulos et al. |
| 2011/0301045 A1 | 12/2011 | He et al. |

(Continued)

FOREIGN PATENT DOCUMENTS

| | | |
|---|---|---|
| WO | WO 2013/188436 | 12/2013 |
| WO | WO 2014/191981 | 12/2014 |

(Continued)

OTHER PUBLICATIONS

International Preliminary Report on Patentability Dated Dec. 17, 2020 From the International Bureau of WIPO Re. Application No. PCT/IL2019/050656. (15 Pages).

(Continued)

*Primary Examiner* — Christian C Boesen

(57) ABSTRACT

A method of detecting an epigenetic DNA modification is described herein, the method comprising: attaching to DNA a labeling agent selective for the DNA modification; contacting an aqueous solution comprising the DNA with at least one addressable region on a surface of a substrate, wherein the addressable region comprises a positively charged substance capable of attaching the DNA to the surface, and the addressable region is surrounded by a hydrophobic region; and determining an amount of labeling agent in the addressable region. Further described herein is a kit comprising a substrate comprising discrete hydrophilic regions separated by a hydrophobic region, and a labeling agent selective for an epigenetic DNA modification; as well as an article of manufacture comprising a substrate comprising a discrete regions separated by a hydrophobic region, a positively charged substance and DNA attached thereto, the DNA comprising such a labeling agent.

13 Claims, 14 Drawing Sheets

(56) References Cited

U.S. PATENT DOCUMENTS

| | | | |
|---|---|---|---|
| 2014/0030727 | A1 | 1/2014 | Pfeifer et al. |
| 2017/0088886 | A1* | 3/2017 | Okura .................. C12Q 1/6827 |
| 2017/0298422 | A1 | 10/2017 | Song et al. |

FOREIGN PATENT DOCUMENTS

| | | |
|---|---|---|
| WO | WO 2015/138405 | 9/2015 |
| WO | WO 2017/081689 | 5/2017 |
| WO | WO 2017/100792 | 6/2017 |
| WO | WO 2019/234753 | 12/2020 |

OTHER PUBLICATIONS

International Search Report and the Written Opinion Dated Aug. 20, 2019 From the International Searching Authority Re. Application No. PCT/IL2019/050656. (15 Pages).
Aran et al. "Comprehensive Analysis of Normal Adjacent to Tumor Transcriptomes", Nature Communications, 8(1): 1077-1-1077-14, Published Online Oct. 20, 2017.
Bachman et al. "5-Hydroxymethylcytosine Is A Predominantly Stable DNA Modification", Nature Chemistry, 6(12): 1049-1055, Dec. 2014.
Buscarlet et al. "Human Blood Cell Levels of 5-Hydroxymethylcytosine (5hmC) Decline With Age, Partly Related to Acquired Mutations in TET2", Experimental Hematology, 44(11): 1042-1084, Published Online Jul. 27, 2016.
Chan et al. "Colorectal Cancer Screening", Singapore Medical Journal, 58(1): 24-28, 2017.
Cui et al. "In Vitro Diagnosis of DNA Methylation Biomarkers With Digital PCR in Breast Tumors", Analyst, 143(13): 3011-3020, Jul. 7, 2018.
De Rosa et al. "Genetics, Diagnosis and Management of Colorectal Cancer (Review)", Oncology Reports, 34(3): 1087-1096, Sep. 2015.
Fearnhead et al. "The ABC of APC", Human Molecular Genetics, 10(7): 721-733, Apr. 2001.
Fernandez et al. "Loss of 5hmC Identifies A New Type of Aberrant DNA Hypermethylation in Glioma", Human Molecular Genetics, 27(17): 3046-3059, Sep. 2018.
Ficz et al. "Dynamic Regulation of 5-Hydroxymethylcytosine in Mouse ES Cells and During Differentiation", Nature, 473(7347): 398-402, May 19, 2011.
Figueroa-Romero et al. "Identification of Epigenetically Altered Genes in Sporadic Amyotrophic Lateral Sclerosis", Plos One, 7(12): e52672-1-e52672-15, Published Online Dec. 26, 2012.
Fleming et al. "Colorectal Carcinoma: Pathologic Aspects", Journal of Gastrointestinal Oncology, 3(3): 153-173, Sep. 2012. (Part I).
Fleming et al. "Colorectal Carcinoma: Pathologic Aspects", Journal of Gastrointestinal Oncology, 3(3): 153-173, Sep. 2012. (Part II).
Fleming et al. "Colorectal Carcinoma: Pathologic Aspects", Journal of Gastrointestinal Oncology, 3(3): 153-173, Sep. 2012. (Part III).
Fleming et al. "Colorectal Carcinoma: Pathologic Aspects", Journal of Gastrointestinal Oncology, 3(3): 153-173, Sep. 2012. (Part IV).
Fleming et al. "Colorectal Carcinoma: Pathologic Aspects", Journal of Gastrointestinal Oncology, 3(3): 153-173, Sep. 2012. (Part V).
Gabrieli et al. "Epigenetic Optical Mapping of 5-Hydroxymethylcystosine in Nanochannel Arrays", ACS Nano, 12(7): 7148-7158, Published Online Jun. 20, 2018.
Galiatsatos et al. "Familial Adenomatous Polyposis", The American Jopurnal of Gastroenterology, 101(2): 385-398, Feb. 1, 2006.
Gilat et al. "Single-Molecule Quantification of 5-Hydroxymethylcytosine for Diagnosis of Blood and Colon Cancers", Clinical Epigenetics, 9(1): 70-1-70-8, Published Online Jul. 14, 2017.
Globisch et al. "Tissue Distribution of 5-Hydroxymethylcytosine and Search for Active Demethylation Intermediates", PLoS One, 5(12): e15367-1-e15367-9, Published Online Dec. 23, 2010.
Guo Lian et al. "Loss of 5-Hydroxymethylcytosine Is An Epigenetic Hallmark of Melanoma", Cell, 150(6): 1135-1146, Sep. 14, 2012.
Haffner et al. "Global 5-Hydroxymethylcytosine Content Is Significantly Reduced in Tissue Stem/Progenitor Cell Compartments and in Human Cancers", Oncotarget, 2(8): 627-637, Published Online Sep. 2, 2011.
Haseeb et al. "Modulation of Ten-eleven Translocation 1 (TET1), Isocitrate Dehydrogenase (IDH) Expression, Alpha-Ketoglutarate (Alpha-KG), and DNA Hydroxymethylation Levels by Interleukin-1 Beta in Primary Human Chondrocytes", The Journal of Biological Chemistry, 289(10): 6877-6885, Mar. 7, 2014.
Heichman et al. "DNA Methylation Biomarkers and Their Utility for Solid Cancer Diagnostics", Clinical Chemistry and Laboratory Medicine, 50(10): 1707-1721, Published online Apr. 28, 2012.
Jenkins et al. "Paternal Aging and Associated Intraindividual Alterations of Global Sperm 5-Methylcytosine and 5-Hydroxymethylcytosine Levels", Fertility and Sterility, 100(4): 945-951, Published Online Jun. 27, 2013.
Jin et al. "5-Hydroxymethylcytosine Is Strongly Depleted in Human Cancers But Its Levels Do Not Correlate With IDH1 Mutations", Cancer Research, 71(24): 73600-7365, Dec. 15, 2011.
Jin et al. "Genomic Mapping of 5-Hydroxymethylcytosine in the Human Brain", Nucleic Acids Research, 39(12): 5015-5024, Published Online Mar. 4, 2011.
Johnson et al. "5-Hydroxymethylcytosine Localizes to Enhancer Elements and Is Associated With Survival in Glioblastoma Patients", Nature Communications, 7(Art.1377): 1-11, Published Online Nov. 25, 2016.
Ko et al. "Impaired Hydroxylation of 5-Methylcytosine in Myeloid Cancers With Mutant TET2", Nature, 468(7325): 839-843, Dec. 9, 2010.
Kraus et al. "Loss of 5-Hydroxymethylcytosine and Intratumoral Heterogeneity as An Epigenomic Hallmark of Glioblastoma", Tumor Biology, 36(11): 8439-8446, Published Online May 29, 2015.
Kriaucionis et al. "The Nuclear DNA Base, 5-Hydroxymethylcytosine Is Present in Brain and Enriched in Purkinje Neurons", Science, 324(5929): 929-930, May 15, 2009.
Kudo et al. "Loss of 5-Hydroxymethylcytosine Is Accompanied With Malignant Cellular Transformation", Cancer Science, 103(4): 670-676, Published Online Feb. 27, 2012.
Li et al. "Distribution of 5-Hydroxymethylcytosine in Different Human Tissues", Journal of Nucleic Acids, 2011(Art.ID 870726): 1-5, Published Online Jun. 9, 2011.
Lin et al. "Correlated 5-Hydroxymethylcystosine (5hmC) and Gene Expression Profiles Underpin Gene and Organ-Specific Epigenetic Regulation in Adult Mouse Brain and Liver", Plos One, 12(1): e170779-1-e170779-25, Published Online Jan. 26, 2017.
Lopez et al. "The Role of 5-Hydroxymethylcytosine in Development, Aging and Age-Related Diseases", Ageing Research Reviews, 37: 28-38, Published Online May 10, 2017.
Michaeli et al. "Optical Detection of Epigenetic Marks: Sensitive Quantificaiton and Direct Imaging of Individual Hydroxymethylcytosine Bases", Chemical Communications, 49(77): 8699-8601, Oct. 7, 2013.
Morey Kinney et al. "Tissue-Specific Distribution and Dynamic Changes of 5-Hydroxymethylcytosine in Mammalian Genomes", The Journal of biological Chemistry, 286(28): 25685-24693, Jul. 15, 2011.
Münzel et al. "Efficient Synthesis of 5-Hydroxymethylcytosine Containing DNA", Organic Letters, 12(24): 5671-5673, Published on Web Nov. 17, 2010.
Münzel et al. "Quantification of the Sixth DNA Base Hydroxymethylcytosine in the Brain", Angewandte Chemie, International Edition in English, 49(31): 5375-5377, Jul. 19, 2010.
Murata et al. "TET Family Proteins and 5-Hydroxymethylcytosine in Esophageal Squamous Cell Carcinoma", Oncotarget, 6(27): 23372-23382, Published Online Jun. 8, 2015.
Nestor et al. "Tissue Type Is A Major Modifier of the 5-Hydroxymethylcytosine Contnet of Human Genes", Genome Research, 22(3): 467-477, Mar. 2012.
Nifker et al. "One-Pot Chemoenzymatic Cascade for Labeling of the Epigenetic Marker 5-Hydroxymethylcytosine", ChemBioChem, 16: 1857-1860, Published Online Jul. 27, 2015.
Orr et al. "Decreased 5-Hydroxymethylcytosine Is Associated With Neural Progenitor Phenotype in Normal Brain and Shorter Survival in Malignant Glioma", PLoS One, 7(7): e41036-1-e41036-11, Published Online Jul. 19, 2012.

(56) References Cited

OTHER PUBLICATIONS

Pirri et al. "Characterization of A Polymeric Adsorbed Coating for DNA Microarray Glass Slides", Analytical Chemistry, 76(5): 1352-1358, Published on Web Jan. 24, 2004.

Ponnaluri et al. "Association of 5-Hydroxymethylation and 5-Methylation of DNA Cystosine With Tissue-Specific Gene Expression", Epigenetics, 12(2): 123-138, Published Online Dec. 2, 2016.

Shahal et al. "Spectroscopic Quantification of 5-Hydroxymethylcytosine in Genomic DNA", Analytical Chemistry, 86(16): 8231-8237, Published Online Jul. 11, 2014.

Shi et al. "New Insights Into 5hmC DNA Modification: Generation, Distribution and Function", Frontiers in Genetics, 8(Art.100): 1-11, Published Online Jul. 19, 2017.

Song et al. "Selective Chemical Labeling Reveals the Genome-Wide Distribution of 5-Hydroxymethylcytosine", Nature Biotechnology, 29(1): 68-72, Jan. 2011.

Stroud et al. "5-Hydroxymethylcytosine Is Associated With Enhancers and Gene Bodies in Human Embryonic Stem Cells", Genome Biology, 12(6): R54-1-R54-8, Jun. 2011.

Tahiliani et al. "Conversion of 5-Methylcytosine to 5-Hydroxymethylcytosine in Mammalian DNA by MLL Partner TET1", Science, 324(5929): 930-935, May 15, 2009.

Van Damme et al. "Characterization of TET and IDH Gene Expression in Chronic Lymphocytic Leukemia: Comparison With Normal B Cells and Prognostic Significance", Clinical Epigenetics, 8(1): 132-1-132-11, Published Online Dec. 7, 2016.

Wossidlo et al. "5-Hydroxymethylcytosine in the Mammalian Zygote Is Linked With Epigenetic Reprogramming", Nature Communications, 2: 241-1-241-8, Published Online Mar. 15, 2011.

Wu et al. "Genome-Wide Analysis of 5-Hydroxymethylcytosine Distribution Reveals Its Dual Function in Transcriptional Regulation in Mouse Embryonic Stem Cells", Genes & Development, 25(7): 679-684, Apr. 2011.

Yang et al. "Tumor Development Is Associated With Decrease of TET Gene Expression and 5-Methylcytosine Hydroxylation", Oncogene, 32(5): 663-669, Jan. 31, 2013.

Zarkov et al. "Novel Glass Slide Preparation System for Single DNA Molecules Analysis", Biotechnology & Biotechnological Equipment, 28(1): 112-117, Published Online May 2, 2014.

Supplementary European Search Report and the European Search Opinion Dated Feb. 17, 2022 From the European Patent Office Re. Application No. 19814416.4. (7 Pages).

* cited by examiner

MULTI-SAMPLE ARRAY CHIP FOR DNA MODIFICATION QUANTIFICATION

RELATED APPLICATIONS

This application is a National Phase of PCT Patent Application No. PCT/IL2019/050656 having International filing date of Jun. 6, 2019, which claims the benefit of priority under 35 USC § 119(e) of U.S. Provisional Application No. 62/681,186 filed on Jun. 6, 2018. The contents of the above applications are all incorporated by reference as if fully set forth herein in their entirety.

The project leading to this application has received funding from the European Research Council (ERC) under the European Union's Horizon 2020 research and innovation program (grant agreement No. 767931).

FIELD AND BACKGROUND OF THE INVENTION

The present invention, in some embodiments thereof, relates to DNA assays and, more particularly, but not exclusively, to a novel methodology for performing quantification of epigenetic DNA modifications.

Epigenetics refers to DNA and chromatic modifications that maintain the underlying DNA sequence. These dynamic, chemical modifications are a major source of genomic variation, yet this variation is difficult to detect by current technologies since it is masked by ensemble averaging. Epigenetic DNA modifications have been reported to exhibit tissue-specific patterns, to correlate with gene regulation and expression, and to be suitable as biomarkers for multiple types of cancer and other syndromes.

Epigenetic modifications include cytosine methylation (5 mC) and the recently discovered cytosine hydroxymethylation (5 hmC), which exhibits tissue and cell type specific distribution in mammalian genomes.

5-Hydroxymethylcytosine (5-hmC) is an epigenetic modification of the DNA base cytosine, recently discovered in mammalian genomes [Tahiliani et al., *Science* 2009, 324:930-935; Kriaucionis & Heintz, *Science* 2009, 324:929-930]. Increasing evidence of the recent years suggests that 5-hmC may have a functional role in gene-expression and dynamic regulation [Ficz et al., *Nature* 2011, 473:398-402; Wossidlo et al., *Nat Commun* 2011, 2:241; Wu et al., *Genes Dev* 2011, 25:679-684; Stroud et al., *Genome Biol* 2011, 12:R54; Kinney et al., *J Biol Chem* 2011, 286:24685-24693], and its global levels were found to be predominantly stable and highly tissue-specific [Bachman et al., *Nat Chem* 2014, 6:1049-1055; Globisch et al., *PLoS One* 2010, 5:e15367; Shahal et al., *Anal Chem* 2014, 86:8231-8237]. A significant global reduction in 5-hmC level was reported for various human cancers, such as melanoma, colorectal, pancreatic, breast, liver, lung, prostate, brain and blood cancers, compared with normal or benign tissues [Haffner et al., *Oncotarget* 2011, 2:627-637; Yang et al., *Oncogene* 2013, 32:663-669; Ko et al., *Nature* 2010, 468:839-843; Johnson et al., *Nat Commun* 2016, 7:13177; Gilat et al., *Clin Epigenet* 2017, 9:70; Orr et al., *PLoS One* 2012, 7:e41036; Li et al., *J Nucleic Acids* 2011, 2011:870726]. Due to this strong correlation between a decreased 5-hmC level and cancer, the modification can serve as a biomarker for the disease.

A standard technique for global quantification is HPLC coupled to mass spectrometry (HPLC-MS) [Jin et al., *Cancer Res* 2011, 71:7360-7365; Munzel et al., *Agnew Chemie* 2010, 49:5375-5377; Buscarlet et al., *Exp Hematol* 2016, 44:1072-1084]. This method is considered accurate, but requires expertise, expensive equipment, time, and large amounts of DNA when assessing tissues with low 5-hmC levels.

Other popular assays are antibody-based assays, such as DNA dot-blot [Ko et al., *Nature* 2010, 468:839-843; Lian et al., *Cell* 2012, 150:1135-1146; Kudo et al., *Cancer Sci* 2012, 103:670-676; Nestor et al., *Genome Res* 2012, 22:467-477; Jin et al., *Nucleic Acids Res* 2011, 39:5015-5024], immunohistochemical (IHC) staining [Haffner et al., *Oncotarget* 2011, 2:627-637; Lian et al., *Cell* 2012, 150:1135-1146; Jin et al., *Cancer Res* 2011, 71:7360-7365; Orr et al., *PLoS One* 2012, 7:e41036; Kudo et al., *Cancer Sci* 2012, 103:670-676; Murata et al., *Oncotarget* 2015, 6:23372-23382] and commercially available enzyme-linked immunosorbent assay (ELISA) kits with anti-5-hmC antibodies [Murata et al., *Oncotarget* 2015, 6:23372-23382; Jenkins et al., *Fertil Steril* 2013, 100:945-951; Haseeb et al, *J Biol Chem* 2014, 289: 6877-6885; Figueroa-Romero et al., *PLoS One* 2012, 7:e52672]. These assays are rather simple, but lack in sensitivity and resolution; meaning they often fail to detect the low 5-hmC levels of some cancerous and healthy tissues, and to differentiate between close levels of different samples.

Studies have shown that T4 β-glucosyltransferase (β-GT) from T-4 bacteriophages can attach a glucose moiety from uridine diphosphoglucose (UDP-Glu) onto the hydroxyl group of 5 hmC, resulting in a glucosylated nucleotide. Song et al. [in *Nature biotechnology*, 2011, 29, 68-72 and U.S. Patent Application having Publication No. 2011/0301045] utilized this enzymatic process to transfer a glucose chemically modified with an azide group onto 5 hmC in genomic DNA. Using Huisgen cycloaddition (click) chemistry, they attached a biotin to the azide group and captured the 5 hmC-containing DNA on streptavidin-coated magnetic beads for sequencing. A commercially available product, the Hydroxymethyl Collector™ (by Active Motif), for detecting and capturing DNA fragments containing 5-hmC methylation, was developed based on this methodology.

International Patent Application Publication WO 2014/191981 describes a method of labeling 5-hmC along a DNA molecule, by attaching a 5-hmC-specific labeling agent to the DNA and extending the DNA molecule. UDP-6-N3-glucose may be used as a reagent modifying 5-hmC with an azide group, which can be further labeled using click chemistry.

International Patent Application Publication WO 2017/081689 describes a method of detecting 5-hmC in DNA at a 5-hmC prevalence lower than 0.002% of total DNA bases, by attaching a 5-hmC labeling agent to the DNA molecule. Diagnosing of cancer by detecting a decrease in 5-hmC levels is also described therein.

Colorectal cancer (CRC) is the third most commonly diagnosed cancer and the third leading cause of cancer mortality in the United States for both men and women.

There is a relatively long period of progression in CRC from polyp to cancer, and screening during this gap allows the detection and removal of adenomas in asymptomatic early-stage CRC [Chan et al., *Singapore Med J* 2017, 58:24-28]. The current golden standard for CRC diagnosis is a complete colonoscopy, coupled with a biopsy for histopathological examination. This procedure allows the tumor localization and possibly the endoscopic excision of polyps [De Rosa et al., *Oncol Rep* 2015, 34:1087-1096]. The histopathological examination of the excised biopsy or polypectomy specimens nowadays is crucial for proper disease staging, choice of therapy, patient management and prognosis assessment. The diagnosis becomes more complicated when this examination reveals rare or controversial histological properties [Fleming et al., *J Gastrointest Oncol* 2012, 3:153-173]. Moreover, these cases demand more of the time of the specialists evaluating the specimens.

Familial adenomatous polyposis (FAP) is an inherited colorectal cancer syndrome, characterized by the onset of hundreds to thousands of adenomatous polyps in the colon and rectum during the second decade of life. FAP is caused by a germline mutation in the adenomatous polyposis coli (APC) gene. APC is a tumor suppressor gene located in chromosome 5, which encodes a large protein with multiple cellular functions and interactions, including roles in signal transduction in the WNT signaling pathway, mediation of intercellular adhesion, stabilization of the cytoskeleton and possibly regulation of the cell cycle and apoptosis.

Untreated, colorectal cancer invariably develops by the early forties of the patients. In order to prevent its onset, progression has to be monitored by timely screening examinations and subsequent treatment [Galiatsatos & Foulkes, *Am J Gastroenterol* 2006, 101:385-398; Fearnhead et al., *Hum Mol Genet* 2010, 10:721-733]. Treatment may be polyp excision or antibiotic treatment.

Additional background art includes Aran et al. [*Nat Commun* 2017, 8:1077]; Cui et al. [*Analyst* 2018, 143:3011-3020]; Fernandez et al. [*Hum Mol Genet* 2018, 27:3046-3059]; Gabrieli et al. [*ACS Nano* 2018, 12:7148-7158]; Heichman & Warren [*Clin Chem Lam Med* 2012, 50:1707-1721]; Kraus et al. [*Tumour Biol* 2015, 36:8439-8446]; Lin et al. [*PLoS ONE* 2017, 12:e0170779]; Lopez et al. [*Ageing Res Rev* 2017, 37:28-38]; Michaeli et al. [*Chem Commun (Camb)* 2013, 49:8599-8601]; Nifker et al. [*ChemBioChem* 2015, 16:1857-1860]; Pirri et al. [*Anal Chem* 2004, 76:1352-1358]; Ponnaluri et al. [*Epigenetics* 2017, 12:123-138]; Shi et al. [*Front Genet* 2017, 8:100]; Van Damme et al. [*Clin Epigenetics* 2016, 8:132]; and Zarkov et al. [*Biotech Biotechnol Equipment* 2014, 28:112-117]; and U.S. Patent Application Publication Nos. 2017/0298422 and 2003/0170689.

SUMMARY OF THE INVENTION

According to an aspect of some embodiments of the invention, there is provided a method of detecting an epigenetic DNA modification, the method comprising:
(a) attaching to a DNA molecule at least one first labeling agent selective for the DNA modification;
(b) contacting an aqueous solution comprising the DNA molecule with at least one addressable region on a surface of a substrate, wherein the addressable region comprises a positively charged substance capable of attaching the DNA molecule to the surface, and the addressable region is surrounded by a hydrophobic region of the surface; and
(c) determining an amount of the at least one first labeling agent in the addressable region, thereby detecting the epigenetic DNA modification.

According to an aspect of some embodiments of the invention, there is provided a method of detecting an epigenetic DNA modification, the method comprising contacting an aqueous solution comprising a DNA molecule having attached (e.g., covalently) thereto at least one first labeling agent selective for the DNA modification with at least one addressable region on a surface of a substrate, wherein the addressable region comprises a positively charged substance capable of attaching the DNA molecule to the surface, and the addressable region is surrounded by a hydrophobic region of the surface, thereby detecting the epigenetic DNA modification.

According to an aspect of some embodiments of the invention, there is provided an article of manufacture comprising a substrate comprising a plurality of discrete regions separated by a hydrophobic region, each of the discrete regions comprising a positively charged substance, wherein in at least a portion of the discrete regions, a DNA molecule is attached to the positively charged substance, and the DNA molecule comprises at least one first labeling agent selective for an epigenetic DNA modification.

According to an aspect of some embodiments of the invention, there is provided a method of detecting an epigenetic DNA modification, the method comprising determining an amount of at least one first labeling agent in an article of manufacture as described herein in any of the respective embodiments and any combination thereof, in at least one of the discrete regions.

According to an aspect of some embodiments of the invention, there is provided a method of diagnosing cancer or pre-malignant lesion in a cell and/or tissue sample, the method comprising:
providing DNA from the cell and/or tissue sample; and
detecting the level of 5-hydroxymethylcytosine residues in the DNA from the cell and/or tissue sample, by a method as described herein in any of the respective embodiments and any combination thereof, wherein the at least one first labeling agent comprises a labeling agent selective for 5-hydroxymethylcytosine,
wherein a significant decrease in the level of 5-hydroxymethylcytosine in the DNA from the cell and/or tissue sample, as compared to a control DNA sample from a healthy cell and/or tissue sample, is indicative of cancer or a pre-malignant lesion.

According to an aspect of some embodiments of the invention, there is provided a method of diagnosing and/or monitoring cancer or pre-malignant lesion in a subject in need thereof, the method comprising:
detecting the level of 5-hydroxymethylcytosine residues in a DNA from a cell of the subject, by a method as described herein in any of the respective embodiments and any combination thereof, wherein the at least one first labeling agent comprises a labeling agent selective for 5-hydroxymethylcytosine,
wherein a significant decrease in the level of 5-hydroxymethylcytosine in the DNA from the subject, as compared to a control DNA sample from a healthy cell and/or tissue sample is indicative that the subject has cancer or a pre-malignant lesion.

According to an aspect of some embodiments of the invention, there is provided a kit comprising:
a substrate comprising a plurality of discrete hydrophilic regions separated by a hydrophobic region; and
at least one labeling agent selective for an epigenetic DNA modification,
wherein the substrate and the labeling agent are preferably packaged individually within the kit.

According to some of any of any of the embodiments of the invention relating to a first labeling agent, the first labeling agent is a fluorescent labeling agent.

According to some of any of any of the embodiments of the invention relating to a method utilizing a first labeling agent, the first labeling agent is a fluorescent labeling agent, and determining an amount of the first labeling agent is effected by detecting fluorescence of the first labeling agent.

According to some of any of any of the embodiments of the invention relating to a method utilizing a first labeling agent, the method further comprises cleaning the surface of the substrate subsequently to attaching the DNA molecule to the surface, and prior to determining an amount of the at least one first labeling agent.

According to some of any of any of the embodiments of the invention relating to cleaning the surface, the cleaning is effected by rinsing with an aqueous liquid.

According to some of any of any of the embodiments of the invention relating to discrete regions, an amount of DNA in each of at least a portion of the discrete regions is in a range of from 5 ng to 300 ng, optionally in a range of from 5 ng to 30 ng, including any intermediate value and subrange therewithin.

According to some of any of any of the embodiments of the invention relating to a method utilizing an aqueous solution comprising DNA, an amount of DNA in the aqueous solution contacted with the addressable region is in a range of from 5 ng to 300 ng, optionally in a range of from 5 ng to 30 ng, including any intermediate value and subrange therewithin.

According to some of any of any of the embodiments of the invention relating to a method utilizing an aqueous solution comprising DNA, a concentration of DNA in the aqueous solution is in a range of from 5 ng/µl to 300 ng/µl, optionally in a range of from 5 ng/µl to 30 ng/µl, including any intermediate value and subrange therewithin.

According to some of any of any of the embodiments of the invention relating to discrete regions, a ratio of an amount of DNA in a discrete region to an area of the discrete region is in a range of from 1 ng/mm$^2$ to 150 ng/mm$^2$, optionally in a range of from 1 ng/mm$^2$ to 15 ng/mm$^2$, including any intermediate value and subrange therewithin.

According to some of any of any of the embodiments of the invention relating to a method utilizing an aqueous solution comprising DNA, a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$, including any intermediate value and subrange therewithin.

According to some of any of any of the embodiments of the invention relating to discrete regions, the discrete regions are separated from one another by a space of at least 1 mm.

According to some of any of any of the embodiments of the invention relating to a method, the method comprises contacting a plurality of addressable regions with an aqueous solution comprising a DNA molecule, the addressable regions separated from each other by a space of at least 1 mm, or of from about 1 mm to about 10 mm or from about 1 mm to about 5 mm, and determining an amount of the at least one first labeling agent in each of the addressable regions.

According to some of any of any of the embodiments of the invention relating to discrete regions, an area of each of at least a portion of the discrete regions is in a range of from 1 mm$^2$ to 10 mm$^2$, including any intermediate value and subrange therewithin.

According to some of any of any of the embodiments of the invention relating to an addressable region, an area of the addressable region is in a range of from 1 mm$^2$ to 10 mm$^2$, including any intermediate value and subrange therewithin.

According to some of any of any of the embodiments of the invention relating to a positively charged substance, the positively charged substance comprises polylysine.

According to some of any of any of the embodiments of the invention relating to an epigenetic DNA modification, the epigenetic DNA modification is selected from the group consisting of a 5-methylcytosine residue, a 5-hydroxymethylcytosine residue, and DNA damage.

According to some of any of any of the embodiments of the invention relating to DNA damage, the DNA damage is characterized by a presence of an 8-oxo-guanine residue and/or a pyrimidine dimer.

According to some of any of any of the embodiments of the invention relating to a DNA molecule, the DNA molecule comprises a plurality of first labeling agents, each of the plurality of first labeling agents being selective for a different type of epigenetic DNA modification.

According to some of any of any of the embodiments of the invention relating to a method, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications.

According to some of any of any of the embodiments of the invention relating to a method, the method further comprises determining an amount of DNA in the addressable region.

According to some of any of any of the embodiments of the invention relating to a DNA molecule, the DNA molecule is further labeled by a second labeling agent.

According to some of any of any of the embodiments of the invention relating to determining an amount of DNA, determining an amount of DNA is effected by contacting the DNA with a second labeling agent, wherein the second labeling agent binds to DNA.

According to some of any of any of the embodiments of the invention relating to a second labeling agent, the second labeling agent is an intercalating agent.

According to some of any of any of the embodiments of the invention relating to determining an amount of DNA, determining an amount of DNA is effected subsequently to determining an amount of the first labeling agent.

According to some of any of any of the embodiments of the invention relating to a substrate, the substrate is a glass substrate.

According to some of any of any of the embodiments of the invention relating to monitoring cancer or pre-malignant lesion, the monitoring comprises monitoring a response of the subject to a treatment.

According to some of any of any of the embodiments of the invention relating to diagnosing and/or monitoring cancer or pre-malignant lesion, a significant increase in the level of 5-hydroxymethylcytosine in the DNA from the subject upon treatment is indicative that the subject is responsive to the treatment.

According to some of any of any of the embodiments of the invention relating to a significant decrease in the level of 5-hydroxymethylcytosine, the significant decrease is to below 50%.

According to some of any of any of the embodiments of the invention relating to DNA, the DNA has a 5-hydroxymethylcytosine prevalence of lower than 0.01%.

According to some of any of any of the embodiments of the invention relating to DNA, the DNA has a 5-hydroxymethylcytosine prevalence of lower than 0.004%.

According to some of any of any of the embodiments of the invention relating to DNA, the DNA has a 5-hydroxymethylcytosine prevalence of lower than 0.001%.

According to some of any of any of the embodiments of the invention relating to discrete hydrophilic regions, at least a portion of the discrete hydrophilic regions comprise a positively charged substance.

According to some of any of any of the embodiments of the invention relating to a kit, the kit further comprises a positively charged substance packaged separately from the substrate.

According to some of any of any of the embodiments of the invention relating to a kit, the kit is for use in detecting an epigenetic DNA modification.

According to some of any of any of the embodiments of the invention relating to an article of manufacture, the article of manufacture is for use in detecting an epigenetic DNA modification.

According to some of any of any of the embodiments of the invention relating to a cancer, the cancer is a soft tissue cancer.

According to some of any of any of the embodiments of the invention relating to a soft tissue cancer, the tissue cancer is selected from the group consisting of leukemia and multiple myeloma.

According to some of any of any of the embodiments of the invention relating to a cancer, the cancer is a solid tumor.

According to some of any of any of the embodiments of the invention relating to a cancer, the cancer is a cancer of the gastrointestinal system (GI) and/or pancreatic cancer.

According to some of any of any of the embodiments of the invention relating to a cancer of the GI system, the cancer of the GI system is selected from the group consisting of colon cancer and rectal cancer.

According to some of any of any of the embodiments of the invention relating to a cancer, the cancer is a soft tissue tumor or a solid tumor and the cell is a PBMC.

According to some of any of any of the embodiments of the invention relating to a cancer, the cancer is a soft tissue tumor or a solid tumor and the cell is a lymphocyte.

According to some of any of any of the embodiments of the invention relating to a pre-malignant lesion, the pre-malignant lesion is an adenomatous polyp.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A presents a 5-hmC (TAMRA fluorescence) channel image of a glass slide (control samples are water in left column, and DNA without labeled 5-hmC (0%) in second-to-left column); FIG. 3B presents a total DNA (EvaGreen® dye fluorescence) channel image of the slide; FIG. 3C presents the fluorescent signal of the 5-hmC (TAMRA) channel as a function of the percentage of labeled 5-hmC in each sample; FIG. 3D presents the fluorescent signal of the total DNA (EvaGreen® dye) channel as a function of the percentage of labeled 5-hmC in each sample; and FIG. 3E presents normalized fluorescent intensity as a function of the percentage of labeled 5-hmC in each sample (error bars represent standard deviation of 5 replicates).

DESCRIPTION OF SPECIFIC EMBODIMENTS OF THE INVENTION

Figure 1:
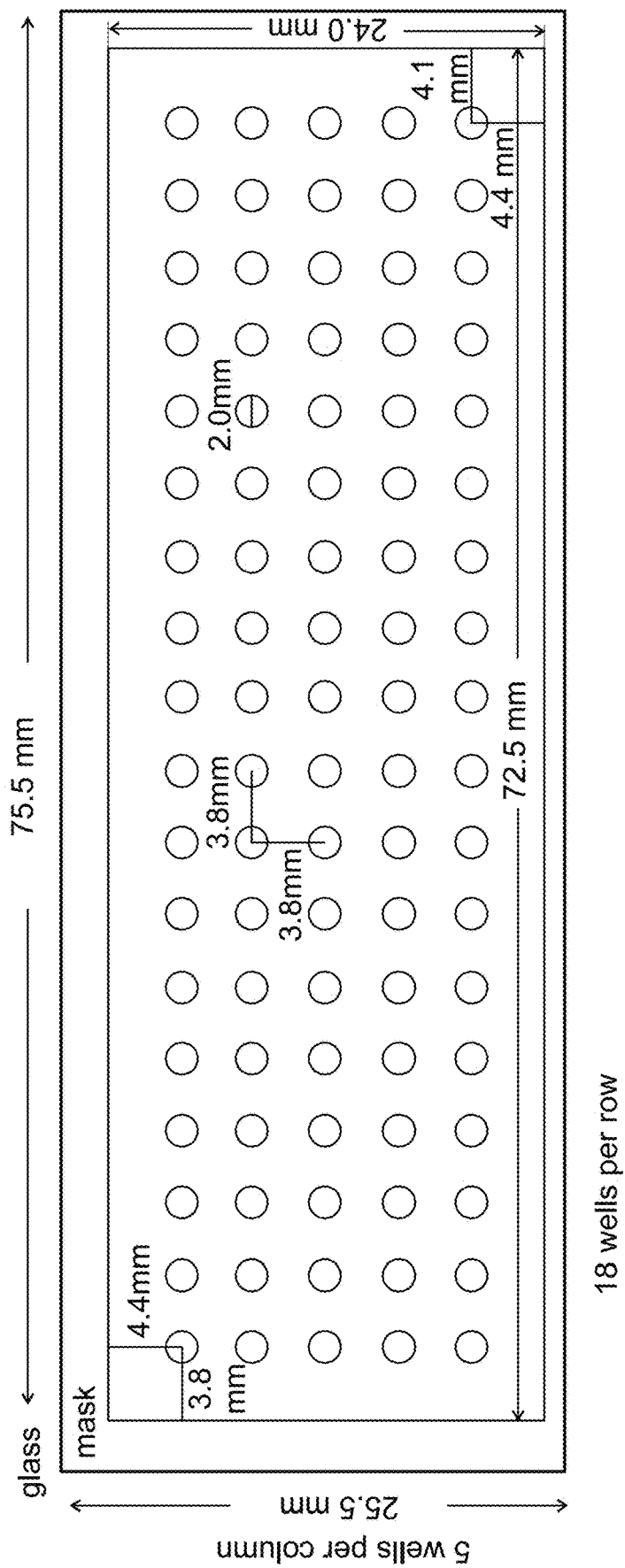
FIG. 1 depicts a multi-well glass substrate according to exemplary embodiments of the invention, in which hydrophilic wells (white circles) are separated by a hydrophobic mask (black).

The present invention, in some embodiments thereof, relates to DNA assays, and more particularly, but not exclusively, to a novel methodology for performing quantification of epigenetic DNA modifications.

The present inventors have determined that a primary obstacle to utilizing DNA biomarkers in sensitive applications (e.g., fluorescence-based applications) is the lack of techniques suitable for analyzing minute amounts of DNA at high throughput and with high sensitivity. Commercially available antibody based kits were tested and failed to deliver the needed sensitivity and reproducibility. Existing platforms such as multi-well plates and plate readers do not have sufficient sensitivity and require large amounts of DNA that is not available for many clinical samples. For example, there are several widespread methods for 5-hmC detection and quantification, yet none seems to fully meet the expectations from diagnostic tools for clinical purposes. Solutions developed for microscopy on the other hand, such as single-molecule slide assays, are low throughput and expensive.

Following laborious experimentation, the present inventors have uncovered a method for global quantification of epigenetic DNA modifications (e.g., in DNA extracted from cells or tissue) such as, but not limited to, 5-methylcytosine (5-mC), 5-hydroxymethylcytosine (5-hmC) residues and DNA damage, which may be effected, for example, on a custom-designed multi-array slide chip. Such a method utilizes optically labeling a DNA modification (e.g., using suitable techniques such as fluorescent labels), followed by placement of a droplet (e.g., from 0.1 to 100 μL in volume) containing labeled DNA on a positively charged addressable region (also referred to herein as a "well") of a substrate (e.g., a glass slide or "chip") which may optionally include many such regions (e.g., in a form of a multi-well array such as a multi-well microscope slide). The droplet is held in place by a hydrophobic mask surrounding the well, and the DNA (which is negatively charged) is attached to the surface of the substrate by attractive electrostatic forces between the positively charged well and the negatively charged DNA, and is preferably not stretched. The presence and/or amount of labeled DNA (labeled with an agent also referred to herein as a "first labeling agent") in each well may then be determined to afford a simple, high-throughput, sensitive tool for the detection and/or quantification of levels of epigenetic modifications in DNA samples upon simple data analysis (e.g., 5-hmC levels in cancer diagnostics).

Optionally, quantification is facilitated by determining the ratio between the amount of labeled DNA and the amount of total DNA in each well. Total DNA may be determined by contacting the DNA with an agent (also referred to herein as a "second labeling agent" or "staining agent") capable of binding to DNA (a procedure also referred to herein as "staining"), preferably in a manner which is relatively independent of DNA sequence, and detecting a signal associated with stained DNA. This is optionally and preferably done using an imaging system, or an imaging spectrometer. In these embodiments, a substrate is firstly imaged when the DNA is unstained (but labeled for the DNA modification or lesion) and is then imaged when the DNA is stained (to thereby quantify the amount of DNA absorbed to the slide) and labeled. Optionally, the first image is acquired through a filter selected to enhance the signal that corresponds to the labeling agent, and the second image is acquired through a filter selected to enhance the signal that corresponds to the staining agent. The signal acquired from the (optionally unstained) labeled DNA correlates with the amount of DNA modifications, and the signal acquired from the stained DNA correlates with the amount of total DNA. The ratio between the two signals can be used as a parameter that quantifies the levels of epigenetic modifications in the DNA. DNA staining can be done using any technique known in the art, such as, but not limited to, using a DNA intercalator (e.g., a fluorescent intercalator).

Herein, binding "in a manner which is relatively independent of DNA sequence" means that the degree of binding (e.g., concentration which binds to DNA) under any given conditions is similar for A, T, C and G nucleotides and/or for A-T and C-G nucleotide pairs. Thus, the degree of binding will not be much affected by the proportion of certain nucleotides in a particular DNA sequence.

Herein throughout, references to "quantification", "quantifying", and the like, are not intended to exclude the possibility of merely determining a presence of a compound, but rather reflect that determining an amount of a compound is frequently (but not necessarily) more useful than merely determining a presence.

While reducing the invention to practice, the inventors have demonstrated the sensitivity and applicability of a high-throughput assay which quantifies 5-hmC levels according to some embodiments of the invention for colorectal and/or pancreatic cancer and/or polyp diagnosis and for monitoring of treatment progression in familial adenomatous polyposis (FAP) patients, suggesting a potential for cancer detection in other models as well. Furthermore, the inventors have confirmed the presence of reduced 5-hmC levels in colorectal and pancreatic cancer, as well as observed a similar reduction in a mouse glioblastoma model. The inventors have further demonstrated the suitability of an assay according to some embodiments of the invention for quantifying DNA damage.

As exemplified herein, the invention can overcome the low levels of epigenetic markers and the low amount of sample available from medical biopsies. For example, 5-hmC at levels of less than 0.004% in DNA samples was successfully quantified.

Without being bound by any particular theory, it is believed that the high sensitivity is associated with concentration of the labeled DNA in the wells (so as to obtain a more readily detectable signal from very small amounts of DNA), localization of the DNA to specific addressable regions (such that a detection apparatus can accurately address the DNA), and/or the ability to remove molecules other than DNA, such as unbound labeling agents (thereby reducing background noise), e.g., by washing of the substrate after attachment of DNA to wells.

In addition, multi-well substrates according to some embodiments of the invention allow for simultaneous measurement of many samples (e.g., several samples from the same patient and/or samples from several patients), thereby enhancing assay robustness and speed. Moreover, the assay is simple, cost-effective, demands minimal expertise and unsophisticated fluorescent equipment. Commercially available slide readers (e.g., fluorescent slide-readers) common in medical facilities and research laboratories may be used, for example, with excellent results. Thus, in some embodiments of the invention, there is provided a kit, e.g., a widespread ready-to-use kit, for performing an assay as described herein.

Commercially available 5-hmC quantification kits have been assessed and found to present low sensitivity, poor reproducibility and even dependency in DNA fragments' length [Gilat et al., *Clin Epigenet* 2017, 9:70].

In contrast, quantification of DNA modifications according to embodiments of the invention may optionally be performed with only nanograms (e.g., 5-30 ng or less) of labeled DNA per well, and can detect DNA modifications (e.g., DNA damage, 5-hydromethylcytosine or 5-methylcytosine) at a prevalence of less than 0.004%, so DNA may optionally be extracted from residual tissue obtained initially for other examinations. For example, in colorectal cancer diagnosis, colonoscopies are routinely performed, coupled with a biopsy for histopathological examination [De Rosa et al., *Oncol Rep* 2015, 34:1087-1096]. The assay described herein could utilize the residual biopsy and extract new molecular information from it. This information is optionally a quantitative value that could localize the patient above or below a threshold that will be determined in a clinical trial. In this way this method could optionally complement histopathological examinations of colon specimens and assist pathologists within the acceptable timescale of sample analysis, mainly when the morphological properties are rare or controversial (e.g., by measuring 5-hmC levels in colon tissue adjacent to a tumor). Furthermore, since regulatory colonoscopies for early detection of CRC are recommended to the average risk population starting the age of 50 [Chan et al., *Singapore Med J* 2017, 58:24-28], an individual's colon 5-hmC level could optionally be compared over time and provide personalized 5-hmC level surveillance.

Additional information that may optionally be obtained from subjects using this method is the 5-hmC level of tissues adjacent to malignant or benign tumors, (e.g., colorectal tumors or polyps). Such tissues are usually not subjected to morphological examination, and their 5-hmC level may be associated with their health. This information may optionally assist in disease staging and in treatment selection.

For example, as exemplified herein, polyps in familial adenomatous polyposis can be distinguished from adjacent normal tissue, the response to treatment can be observed as changes in DNA from the polyp (to a state closer to that of DNA from normal tissue). This may optionally facilitate more personalized medicine and individual treatment selection.

Blood is a very accessible tissue for diagnostic purposes, but the very low 5-hmC levels found in blood (~0.002% in healthy individuals, and as low as 0.0005% for some blood cancers) have made 5-hmC-based assays unsuitable so far for blood assessments in practical applications.

Currently, no available method enables facile, accurate and non-expensive detection of 5-hmC levels in samples with very low 5-hmC levels, such as blood samples, and specifically in blood cancer samples. When a commercial ELISA kit was employed to evaluate 5-hmC levels in the blood of chronic lymphocytic leukemia (CLL) patients and healthy individuals, no significant difference was reported [Van Damme et al., *Clin Epigenetics* 2016, 8:132]. However, this reported result may merely reflect insufficient sensitivity of the assay rather than actual 5-hmC levels in the samples [Gilat et al., *Clin Epigenet* 2017, 9:70].

In contrast, the ability to detect different 5-hmC levels in healthy and cancerous blood samples is exemplified herein, even with small amounts of DNA (e.g., as little as about 30 ng). Embodiments of the invention offer an improvement to the techniques and timescales currently used in the field of blood cancer diagnostics.

In addition to the clinical potential described herein, embodiments of the invention may also be useful for research purposes, for example, in exploring correlation between altered levels of DNA modifications and various conditions (e.g., other than cancer), or the role of 5-hmC in such conditions.

Up to date, the best prognosis in colorectal cancer is achieved by early detection and screening of the total population for premalignant and early stage tumors. However, a major bottleneck in the process of colorectal sample analysis is the pathological examination, which is carried out manually and often does not provide clear and definite results. Embodiments of the invention may be used to assist pathologists, in cases where traditional examination is inconclusive (such as premalignant or adjacent tissue), by adding another layer of quantitative molecular information. Assays according to some embodiments of the invention provide an absolute physical measure of 5 mC and 5 hmC levels by covalent labeling and fluorescence detection. The relatively high dynamic range of colorectal cancer coupled with a quantitative measure may allow staging of the disease and may also be indicative as a measure for response to therapy.

According to an aspect of some embodiments of the invention, there is provided a method of detecting an epigenetic DNA modification, the method comprising contacting an aqueous solution comprising a DNA molecule having attached thereto (e.g., covalently attached thereto) at least one labeling agent selective for the DNA modification (which agent is referred to herein interchangeably as a "first labeling agent") with at least one addressable region on a surface of a substrate (e.g., a glass substrate), wherein the addressable region comprises a positively charged substance capable of attaching the DNA molecule to the surface (e.g., via attachment of DNA to the positively charged substance).

Herein, the term "detecting" encompasses determining a presence and/or determining an amount.

In some of any of the respective embodiments described herein, detecting an epigenetic DNA modification comprises determining an amount of an epigenetic DNA modification.

According to some of any of the respective embodiments described herein, the method comprises:
(a) contacting an aqueous solution comprising a DNA molecule having attached thereto at least one first labeling agent with at least one addressable region on a surface of a substrate, according to any of the respective embodiments described herein; and
(b) determining a presence and/or an amount of at least one first labeling agent in the addressable region, thereby detecting the epigenetic DNA modification.

In some of any of the respective embodiments described herein, the method comprises determining an amount of at least one first labeling agent in the addressable region.

In some embodiments, the method comprises:
(a) attaching to a DNA molecule at least one labeling agent selective for the DNA modification (which agent is referred to herein interchangeably as a "first labeling agent");
(b) contacting an aqueous solution comprising the DNA molecule with at least one addressable region on a surface of a substrate (e.g., a glass substrate), wherein the addressable region comprises a positively charged substance capable of attaching the DNA molecule to the surface (e.g., via attachment of DNA to the positively charged substance); and
(c) determining a presence and/or an amount (e.g., determining an amount) of at least one first labeling agent in the addressable region.

The addressable region is preferably surrounded by a hydrophobic region of the surface.

In some embodiments of any of the embodiments described herein, the DNA molecule is a double stranded DNA molecule.

In some embodiments of any of the embodiments described herein relating to attachment of a DNA molecule to a surface, the DNA molecule is free to contact the surface. In some of any of the embodiments described herein, the DNA is attached directly to the surface. Thus, for example, attachment of a cell (which comprises DNA) to a surface is not considered herein to be attachment of DNA to a surface.

In some embodiments, the aqueous solution comprising the DNA is substantially devoid of cells.

In some embodiments of any of the embodiments described herein relating to attachment of a DNA molecule to a surface, the DNA molecule is attached to the surface by non-covalent bonds, for example, electrostatic interactions between (negatively charged) DNA and the positively charged substance at the surface.

In some embodiments of any of the embodiments described herein relating to attachment of a DNA molecule to a surface, the attached DNA molecule is not stretched.

Herein, the phrases "epigenetic DNA modification" and "epigenetic modification" (which are used herein interchangeably) refer to modifications of DNA which do not affect the DNA sequence, that is, they do not comprise replacement of one standard nucleotide (A, C, G or T) with another such nucleotide.

Examples of epigenetic DNA modification that may be detected according to embodiments of the invention include, without limitation, a 5-methylcytosine residue and/or a 5-hydroxymethylcytosine residue (which may be regarded as epigenetic modifications of cytosine (C)), and DNA damage (e.g., DNA lesions), optionally single strand DNA damage (e.g., abasic sites (missing purine or pyrimidine base), single strand breaks, pyrimidine dimers such as cyclobutane dimers and/or 6-4 pyrimidone photoproducts, and oxidized nucleotides). Exemplary labeling agents for labeling 5-methylcytosine residue and single strand DNA damage are exemplified herein.

The phrase "labeling agent" refers to an agent capable of attaching to a target molecule (e.g., a DNA molecule) so as to form a readily detectable derivative of the target molecule. The labeling agent typically comprises a detectable moiety (e.g., a fluorescent moiety, a chromophore, and/or a radioactive isotope) or a detectable moiety is formed upon attachment of the labeling agent to the target molecule.

Attaching a labeling agent to a DNA molecule (according to any of the respective embodiments described herein) may optionally be effected using suitable reagents, such as are known in the art.

In some embodiments of any of the embodiments described herein relating to a labeling agent, the labeling agent (according to any of the respective embodiments described herein) is a fluorescent labeling agent. In some embodiments, determining an amount of a labeling agent (according to any of the respective embodiments described herein) is effected by detecting fluorescence of the labeling agent.

In some embodiments of any of the embodiments described herein, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications. In such embodiments, the different first labeling agents are optionally characterized by different absorption, excitation and/or emission wavelengths.

In some embodiments of any of the embodiments described herein, attaching a first labeling agent to a DNA molecule (e.g., one of a plurality of first labeling agents) is effected by contacting the DNA with an enzyme which specifically removes a modified DNA nucleobase and/or nucleotide, at least one repair enzyme for replacing the removed DNA nucleobase and/or nucleotide, and a labeled (e.g., fluorescently labeled) DNA nucleobase and/or nucleotide suitable for replacing the removed DNA nucleobase and/or nucleotide. For example, OGG1 (oxoguanine glycosylase 1)—e.g., human OGG1—may optionally be used for specifically labeling 8-oxo-guanine residues (e.g., by removing 8-oxo-guanine, thereby allowing its replacement with a labeled nucleobase); and PDG (pyrimidine dimer glycosylase)—e.g., T4 bacteriophage PDG—may optionally be used to specifically label pyrimidine dimers (e.g., by removing pyrimidine dimers, thereby allowing their replacement with labeled nucleobases).

In some embodiments of any of the embodiments described herein, the method further comprises cleaning the surface of the substrate (e.g., so as to remove labeling agent which is not bound to DNA) subsequently to attaching the DNA molecule to the surface, and prior to determining an amount of the at least one first labeling agent. In some embodiments, cleaning the surface is effected by rinsing with a liquid, e.g., an aqueous liquid.

In some embodiments of any of the embodiments described herein, an area of the addressable region is at least 1 $mm^2$, optionally in a range of from 1 $mm^2$ to 10 $mm^2$, including any intermediate value and subrange therewithin. In some embodiments, an area of the addressable region is at least 3 $mm^2$, optionally in a range of from 3 $mm^2$ to 10 $mm^2$, including any intermediate value and subrange therewithin.

In some embodiments of any of the embodiments described herein, an amount of DNA in the aqueous solution contacted with the addressable region is in a range of from 5 ng to 300 ng, optionally in a range of from 5 ng to 30 ng, and optionally in a range of from 5 ng to 15 ng, including any intermediate value and subrange therewithin. In some embodiments, an amount of DNA in the aqueous solution contacted with the addressable region is in a range of from 15 ng to 300 ng, optionally in a range of from 15 ng to 30 ng, including any intermediate value and subrange therewithin.

In some embodiments of any of the embodiments described herein, a concentration of DNA in the aqueous solution contacted with the addressable region is in a range of from 5 ng/$\mu$l to 300 ng/$\mu$l, optionally in a range of from 5 ng/$\mu$l to 30 ng/$\mu$l, and optionally in a range of from 5 ng/$\mu$l to 15 ng/$\mu$l, including any intermediate value and subrange therewithin. In some embodiments, a concentration of DNA in the aqueous solution contacted with the addressable region is in a range of from 15 ng/$\mu$l to 300 ng/$\mu$l, optionally in a range of from 15 ng/$\mu$l to 30 ng/$\mu$l, including any intermediate value and subrange therewithin.

In some embodiments of any of the embodiments described herein, a ratio of an amount of DNA in the aqueous solution contacted with the addressable region to an area of the addressable region is in a range of from 1 ng/$mm^2$ to 150 ng/$mm^2$, optionally in a range of from 1 ng/$mm^2$ to 15 ng/$mm^2$, including any intermediate value and subrange therewithin. In some embodiments, a ratio of an amount of DNA in the aqueous solution contacted with the addressable region to an area of the addressable region is in a range of from 3 ng/$mm^2$ to 150 ng/$mm^2$, optionally in a range of from 3 ng/$mm^2$ to 15 ng/$mm^2$, including any intermediate value and subrange therewithin.

In some embodiments of any of the embodiments described herein, the method comprises contacting a plurality of addressable regions with an aqueous solution comprising a DNA molecule. In some such embodiments, the method further comprises determining an amount of first labeling agent(s) in at least a portion of each of the addressable regions.

In some embodiments of any of the embodiments described herein relating to a plurality of addressable regions, the addressable regions separated from each other by a space of at least 1 mm, or of from about 1 mm to about 10 mm, or from about 1 mm to about 5 mm.

The positively charged substance may be any suitable positively charged substance known in the art for use in facilitating DNA attachment to a surface. Polylysine is an exemplary positively charged substance. Additional positively charged substances include, without limitation, cationic detergents, polyhistidine and aminosilanes.

In some embodiments of any of the embodiments described herein, the substrate is in a form of a slide (e.g., a glass slide), for example, a slide such as used for microscopic observation.

The slide is optionally configured to be readable by a commercial optical slide reader.

In some embodiments of any of the embodiments described herein, the method further comprises determining an amount of DNA in an addressable region. Determining an amount of DNA may be effected according to any suitable technique known in the art.

In some embodiments of any of the embodiments described herein, determining an amount of DNA is effected by contacting the DNA with a second labeling agent (e.g., a fluorescent agent), wherein the second labeling agent binds to DNA (preferably in a manner which is independent of the DNA sequence and the amount of epigenetic modifications therein). In some such embodiments, determining an amount of DNA (e.g., contacting the DNA with a second labeling agent) is effected subsequently to determining an amount of first labeling agent(s) (according to any of the respective embodiments described herein). In some embodiments, the second labeling agent binds to DNA non-covalently.

The second labeling agent may be any agent known in the art to be suitable for labeling DNA (according to any of the respective embodiments described herein), and is a different agent from the first labeling agent(s) used as described herein. The first labeling agent(s) and second labeling agent may optionally differ from each other by being of different labeling types, for example, wherein one labeling agent is a fluorescent labeling agent and another labeling agent is detected by a different technique, for example, a radioactive label or a chromophore-containing label detected by absorption spectroscopy. Alternatively or additionally, may first labeling agent(s) and second labeling agent may optionally be detected by similar technique, but differ in certain parameters, e.g., wherein the first and second labeling agents are optionally characterized by different absorption, excitation and/or emission wavelengths.

A signal (e.g., a fluorescence spectroscopy or absorption spectroscopy signal) of any given labeling agent is optionally enhanced by use of one or more suitable filters (e.g., enhancement of sensitivity by reducing background noise) selective for a signal of the labeling agent (e.g., selective for an emission or excitation wavelength). The skilled person will also know how to utilize suitable filters to detect simultaneously signals of multiple labeling agents.

In some embodiments of any of the embodiments described herein, the second labeling agent is an intercalating agent, that is, an agent which naturally fits between two base pairs in DNA. Intercalating agents are usually planar molecules (e.g., polycyclic aromatic agents), and of an appropriate size (e.g., similar in size to a DNA base pair).

According to an aspect of some embodiments of the invention, there is provided an article of manufacture comprising a substrate, the substrate comprising a plurality of discrete regions separated by a hydrophobic region of, each of the discrete regions comprising a positively charged substance, wherein in at least a portion of the discrete regions, a DNA molecule is attached to the positively charged substance, and the DNA molecule comprises at least one first labeling agent selective for an epigenetic DNA modification.

In some embodiments of any of the embodiments described herein, the first labeling agent is a fluorescent labeling agent.

In some embodiments of any of the embodiments described herein, the substrate is a glass substrate.

In some embodiments of any of the embodiments described herein, an area of each of at least a portion of the discrete regions is in a range of from 1 mm$^2$ to 10 mm$^2$ (e.g., from 1 mm$^2$ to 3 mm$^2$, or from 3 mm$^2$ to 10 mm$^2$), including any intermediate value and subrange therewithin.

In some embodiments of any of the embodiments described herein, an amount of DNA in each of at least a portion of the discrete regions is in a range of from 5 ng to 300 ng (e.g., from 5 to 15 ng, or from 15 to 300 ng), optionally in a range of from 5 ng to 30 ng (e.g., from 15 to 30 ng), including any intermediate value and subrange therewithin.

In some embodiments of any of the embodiments described herein, a ratio of an amount of DNA in a discrete region to an area of the discrete region is in a range of from 1 ng/mm$^2$ to 150 ng/mm$^2$ (e.g., from 1 to 3 ng/mm$^2$, or from 3 to 150 nm/mm$^2$), optionally in a range of from 1 ng/mm$^2$ to 15 ng/mm$^2$ (e.g., from 3 to 15 ng/mm$^2$), including any intermediate value and subrange therewithin.

In some embodiments of any of the embodiments described herein, the discrete regions are separated from one another by a space of at least 1 mm, or at least 2 mm, or at least 3 mm.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the DNA molecule comprises a plurality of first labeling agents, each of the plurality of first labeling agents being selective for a different type of epigenetic DNA modification.

In some embodiments of any of the embodiments described herein, the DNA molecule is further labeled by a second labeling agent (according to any of the respective embodiments described herein).

In some embodiments of any of the embodiments described herein, the second labeling agent is an intercalating agent.

In some embodiments of any of the embodiments described herein, the article of manufacture (according to any of the respective embodiments described herein) is for use in detecting an epigenetic DNA modification.

According to an aspect of some embodiments of the invention, there is provided a method of detecting an epigenetic DNA modification, the method comprising determining an amount of at least one of the first labeling agent in an article of manufacture according to any of the respective embodiments described herein, in at least one of the discrete regions.

According to an aspect of some embodiments of the invention, there is provided a method of diagnosing cancer or pre-malignant lesion in a cell and/or tissue sample, the method comprising:
providing DNA from the cell and/or tissue sample; and
detecting the level of 5-hydroxymethylcytosine residues in the DNA from the cell and/or tissue sample, by a method according to any of the respective embodiments described herein, wherein the at least one first labeling agent comprises a labeling agent selective for 5-hydroxymethylcytosine,
wherein a significant decrease in the level of 5-hydroxymethylcytosine in the DNA from the cell and/or tissue sample, as compared to a control DNA sample from a healthy cell and/or tissue sample is indicative of cancer or a pre-malignant lesion.

According to an aspect of some embodiments of the invention, there is provided a method of diagnosing and/or monitoring cancer or pre-malignant lesion in a subject in need thereof, the method comprising:
detecting the level of 5-hydroxymethylcytosine residues in a DNA from a cell of the subject, by a method according to any of the respective embodiments described herein, wherein the at least one first labeling agent comprises a labeling agent selective for 5-hydroxymethylcytosine,
wherein a significant decrease in the level of 5-hydroxymethylcytosine in the DNA from the subject, as compared to a control DNA sample from a healthy cell and/or tissue sample is indicative that the subject has cancer or a pre-malignant lesion.

In some embodiments of any of the embodiments described herein, the monitoring comprises recovery of a subject.

In some embodiments of any of the embodiments described herein, the monitoring comprises monitoring a response of the subject to a treatment.

In some embodiments of any of the embodiments described herein, a significant increase in the level of 5-hydroxymethylcytosine in the DNA from the subject upon treatment is indicative that the subject is responsive to the treatment.

In some embodiments of any of the embodiments described herein, a significant decrease is to below 50%.

In some embodiments of any of the embodiments described herein, the DNA has a 5-hydroxymethylcytosine prevalence of lower than 0.01%.

In some embodiments of any of the embodiments described herein, the DNA has a 5-hydroxymethylcytosine prevalence of lower than 0.004%.

In some embodiments of any of the embodiments described herein, the DNA has a 5-hydroxymethylcytosine prevalence of lower than 0.001%.

In some embodiments of any of the embodiments described herein, the cancer is a soft tissue cancer. In some embodiments, the soft tissue cancer is selected from the group consisting of leukemia and multiple myeloma.

In some embodiments of any of the embodiments described herein, the cancer is a solid tumor.

In some embodiments of any of the embodiments described herein, the cancer is pancreatic cancer.

In some embodiments of any of the embodiments described herein, the cancer is of the gastrointestinal system (GI). In some embodiments, the cancer of the GI system is selected from the group consisting of colon cancer and rectal cancer.

In some embodiments of any of the embodiments described herein, the cancer is a soft tissue tumor or a solid tumor and the cell is a PBMC (peripheral blood mononuclear cell).

In some embodiments of any of the embodiments described herein, the cancer is a soft tissue tumor or a solid tumor and the cell is a lymphocyte.

In some embodiments of any of the embodiments described herein, the pre-malignant lesion is an adenomatous polyp.

According to an aspect of some embodiments of the invention, there is provided a kit comprising:
- a substrate comprising a plurality of discrete hydrophilic regions, preferably separated by a hydrophobic region; and
- at least one first labeling agent (selective for an epigenetic DNA modification).

The substrate and the labeling agent in the kit are preferably packaged individually within the kit.

In some embodiments of any of the embodiments described herein, at least a portion of the discrete hydrophilic regions comprise a positively charged substance.

In some embodiments of any of the embodiments described herein, the kit further comprises a second labeling agent (according to any of the respective embodiments described herein).

In some embodiments of any of the embodiments described herein, the kit further comprises instructions for using a second labeling agent to determine an amount of DNA in a region (according to any of the respective embodiments described herein), for example, packaged individually within the kit.

In some embodiments of any of the embodiments described herein, the kit further comprises a liquid for cleaning the substrate according to any of the respective embodiments described herein, for example, packaged individually within the kit.

In some embodiments of any of the embodiments described herein, the kit further comprises a positively charged substance packaged separately from the substrate, for example, packaged individually within the kit. Optionally, the kit further comprises instructions for applying the positively charged substances to discrete regions of the substrate.

In some embodiments of any of the embodiments described herein, the kit is for use in detecting an epigenetic DNA modification, e.g., by a method according to any of the respective embodiments described herein.

In some embodiments of any of the embodiments described herein, the kit further comprises (e.g., in or on a packaging) instructions for detecting an epigenetic DNA modification, e.g., by a method according to any of the respective embodiments described herein.

According to an aspect of some embodiments of the invention, there is provided a method of detecting an epigenetic DNA modification, the method comprising:
(a) attaching to a DNA molecule at least one first labeling agent selective for the DNA modification;
(b) contacting an aqueous solution comprising the DNA molecule with at least one addressable region on a surface of a substrate, wherein the addressable region comprises a positively charged substance capable of attaching the DNA molecule to the surface, and the addressable region is surrounded by a hydrophobic region of the surface, and, subsequent to contacting, cleaning the surface of the substrate; and
(c) determining an amount of the at least one first labeling agent in the addressable region.

In some embodiments of any of the embodiments described herein, the first labeling agent is a fluorescent labeling agent, and determining an amount of the labeling agent is effected by detecting fluorescence of the first labeling agent.

In some embodiments of any of the embodiments described herein, cleaning is effected by rinsing with an aqueous liquid.

In some embodiments of any of the embodiments described herein, an amount of DNA in the aqueous solution contacted with the addressable region is in a range of from 5 ng to 300 ng, optionally in a range of from 5 ng to 30 ng, including any intermediate value and subrange therewithin (e.g., according to any of the respective embodiments described herein).

In some embodiments of any of the embodiments described herein, a concentration of DNA in the aqueous solution is in a range of from 5 ng/µl to 300 ng/µl, optionally in a range of from 5 ng/µl to 30 ng/µl, including any intermediate value and subrange therewithin (e.g., according to any of the respective embodiments described herein).

In some embodiments of any of the embodiments described herein, a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$, including any intermediate value and subrange therewithin (e.g., according to any of the respective embodiments described herein).

In some embodiments of any of the embodiments described herein, an area of the addressable region is in a range of from 1 mm$^2$ to 10 mm$^2$, including any intermediate value and subrange therewithin (e.g., according to any of the respective embodiments described herein).

In some embodiments of any of the embodiments described herein, the method comprises contacting a plurality of addressable regions with an aqueous solution comprising a DNA molecule, the addressable regions being separated from each other by a space of at least 1 mm (e.g., according to any of the respective embodiments described herein), and determining an amount of the at least one first labeling agent in each of the addressable regions.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications.

In some embodiments of any of the embodiments described herein, the method further comprises determining an amount of DNA in the addressable region.

In some embodiments of any of the embodiments described herein, determining an amount of DNA is effected by contacting the DNA with a second labeling agent (according to any of the respective embodiments described herein), optionally an intercalating agent.

In some embodiments of any of the embodiments described herein, determining an amount of DNA is effected subsequently to determining an amount of first labeling agent(s).

According to an aspect of some embodiments of the invention, there is provided a method of detecting an epigenetic DNA modification, the method comprising:
(a) attaching to a DNA molecule at least one first labeling agent selective for the DNA modification;
(b) contacting an aqueous solution comprising the DNA molecule with at least one addressable region on a surface of a substrate, wherein a concentration of DNA in the aqueous solution is in a range of from 5 ng/µl to 300 ng/µl, optionally in a range of from 5 ng/µl to 30 ng/µl (including any intermediate value and subrange therewithin), and wherein the addressable region comprises a positively charged substance capable of attaching the DNA molecule to the surface, and the addressable region is surrounded by a hydrophobic region of the surface; and
(c) determining an amount of the at least one first labeling agent in the addressable region.

In some embodiments of any of the embodiments described herein, the first labeling agent is a fluorescent labeling agent, and determining an amount of the labeling agent is effected by detecting fluorescence of the first labeling agent.

In some embodiments of any of the embodiments described herein, the method comprises cleaning the surface of the substrate subsequently to attaching the DNA molecule to the surface, and prior to determining an amount of the at least one first labeling agent.

In some embodiments of any of the embodiments described herein, cleaning is effected by rinsing with an aqueous liquid.

In some embodiments of any of the embodiments described herein, an amount of DNA in the aqueous solution contacted with the addressable region is in a range of from 5 ng to 300 ng, optionally in a range of from 5 ng to 30 ng, including any intermediate value and subrange therewithin (e.g., according to any of the respective embodiments described herein).

In some embodiments of any of the embodiments described herein, a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$, including any intermediate value and subrange therewithin (e.g., according to any of the respective embodiments described herein).

In some embodiments of any of the embodiments described herein, an area of the addressable region is in a range of from 1 mm$^2$ to 10 mm$^2$, including any intermediate value and subrange therewithin (e.g., according to any of the respective embodiments described herein).

In some embodiments of any of the embodiments described herein, the method comprises contacting a plurality of addressable regions with an aqueous solution comprising a DNA molecule, the addressable regions being separated from each other by a space of at least 1 mm (e.g., according to any of the respective embodiments described herein), and determining an amount of the at least one first labeling agent in each of the addressable regions.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications.

In some embodiments of any of the embodiments described herein, the method further comprises determining an amount of DNA in the addressable region.

In some embodiments of any of the embodiments described herein, determining an amount of DNA is effected by contacting the DNA with a second labeling agent (according to any of the respective embodiments described herein), optionally an intercalating agent.

In some embodiments of any of the embodiments described herein, determining an amount of DNA is effected subsequently to determining an amount of first labeling agent(s).

According to an aspect of some embodiments of the invention, there is provided a method of detecting an epigenetic DNA modification, the method comprising:
(a) attaching to a DNA molecule at least one first labeling agent selective for the DNA modification;
(b) contacting an aqueous solution comprising the DNA molecule with at least one addressable region on a surface of a substrate, wherein an amount of DNA in the aqueous solution contacted with the addressable region is in a range of from 5 ng to 300 ng, optionally in a range of from 5 ng to 30 ng (including any intermediate value and subrange therewithin), and wherein the addressable region comprises a positively charged substance capable of attaching the DNA molecule to the surface, and the addressable region is surrounded by a hydrophobic region of the surface; and
(c) determining an amount of the at least one first labeling agent in the addressable region.

In some embodiments of any of the embodiments described herein, the first labeling agent is a fluorescent labeling agent, and determining an amount of the labeling agent is effected by detecting fluorescence of the first labeling agent.

In some embodiments of any of the embodiments described herein, the method comprises cleaning the surface of the substrate subsequently to attaching the DNA molecule to the surface, and prior to determining an amount of the at least one first labeling agent.

In some embodiments of any of the embodiments described herein, cleaning is effected by rinsing with an aqueous liquid.

In some embodiments of any of the embodiments described herein, a concentration of DNA in the aqueous solution is in a range of from 5 ng/µl to 300 ng/µl, optionally in a range of from 5 ng/µl to 30 ng/µl, including any intermediate value and subrange therewithin (e.g., according to any of the respective embodiments described herein).

In some embodiments of any of the embodiments described herein, a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$, including any intermediate value and subrange therewithin (e.g., according to any of the respective embodiments described herein).

In some embodiments of any of the embodiments described herein, an area of the addressable region is in a range of from 1 mm$^2$ to 10 mm$^2$, including any intermediate value and subrange therewithin (e.g., according to any of the respective embodiments described herein).

In some embodiments of any of the embodiments described herein, the method comprises contacting a plurality of addressable regions with an aqueous solution comprising a DNA molecule, the addressable regions being separated from each other by a space of at least 1 mm, and determining an amount of the at least one first labeling agent in each of the addressable regions.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications.

In some embodiments of any of the embodiments described herein, the method further comprises determining an amount of DNA in the addressable region.

In some embodiments of any of the embodiments described herein, determining an amount of DNA is effected by contacting the DNA with a second labeling agent (according to any of the respective embodiments described herein), optionally an intercalating agent.

In some embodiments of any of the embodiments described herein, determining an amount of DNA is effected subsequently to determining an amount of first labeling agent(s).

According to an aspect of some embodiments of the invention, there is provided an article of manufacture comprising a substrate, the substrate comprising a plurality of discrete regions separated by a hydrophobic region, each of the discrete regions comprising a positively charged substance, wherein in at least a portion of the discrete regions, a DNA molecule is attached to the positively charged substance, and the DNA molecule comprises at least one first labeling agent selective for an epigenetic DNA modification, and wherein an amount of DNA in each of at least a portion of the discrete regions is in a range of from 5 ng to 300 ng, optionally in a range of from 5 ng to 30 ng, including any intermediate value and subrange therewithin (e.g., according to any of the respective embodiments described herein).

In some embodiments of any of the embodiments described herein, the first labeling agent is a fluorescent labeling agent.

In some embodiments of any of the embodiments described herein, the substrate is a glass substrate.

In some embodiments of any of the embodiments described herein, a ratio of an amount of DNA in a discrete region to an area of the discrete region is in a range of from 1 ng/mm$^2$ to 150 ng/mm$^2$, optionally in a range of from 1 ng/mm$^2$ to 15 ng/mm$^2$, including any intermediate value and subrange therewithin (e.g., according to any of the respective embodiments described herein).

In some embodiments of any of the embodiments described herein, an area of each of at least a portion of the discrete regions is in a range of from 1 mm$^2$ to 10 mm$^2$, including any intermediate value and subrange therewithin (e.g., according to any of the respective embodiments described herein).

In some embodiments of any of the embodiments described herein, the discrete regions are separated from one another by a space of at least 1 mm.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the DNA molecule comprises a plurality of first labeling agents, each of the plurality of first labeling agents being selective for a different type of epigenetic DNA modification.

In some embodiments of any of the embodiments described herein, the DNA molecule is further labeled by a second labeling agent (according to any of the respective embodiments described herein), optionally an intercalating agent.

In some embodiments of any of the embodiments described herein, the article of manufacture is for use in detecting an epigenetic DNA modification.

According to an aspect of some embodiments of the invention, there is provided a method of detecting an epigenetic DNA modification, the method comprising:
  (a) attaching to a DNA molecule at least one first labeling agent (selective for a DNA modification);
  (b) contacting an aqueous solution comprising the DNA molecule with at least one addressable region on a surface of a substrate, wherein the addressable region comprises a positively charged substance capable of attaching the DNA molecule to the surface, and the addressable region is surrounded by a hydrophobic region of the surface, and wherein a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$ (including any intermediate value and subrange therewithin); and
  (c) determining an amount of the at least one first labeling agent in the addressable region.

In some embodiments of any of the embodiments described herein, the first labeling agent is a fluorescent labeling agent, and determining an amount of the labeling agent is effected by detecting fluorescence of the first labeling agent.

In some embodiments of any of the embodiments described herein, the method comprises cleaning the surface of the substrate subsequently to attaching the DNA molecule to the surface, and prior to determining an amount of the at least one first labeling agent.

In some embodiments of any of the embodiments described herein, cleaning is effected by rinsing with an aqueous liquid.

In some embodiments of any of the embodiments described herein, an amount of DNA in the aqueous solution contacted with the addressable region is in a range of from 5 ng to 300 ng, optionally in a range of from 5 ng to 30 ng, including any intermediate value and subrange therewithin (e.g., according to any of the respective embodiments described herein).

In some embodiments of any of the embodiments described herein, a concentration of DNA in the aqueous solution is in a range of from 5 ng/μl to 300 ng/μl, optionally in a range of from 5 ng/μl to 30 ng/μl, including any intermediate value and subrange therewithin (e.g., according to any of the respective embodiments described herein).

In some embodiments of any of the embodiments described herein, an area of the addressable region is in a range of from 1 mm$^2$ to 10 mm$^2$, including any intermediate value and subrange therewithin (e.g., according to any of the respective embodiments described herein).

In some embodiments of any of the embodiments described herein, the method comprises contacting a plurality of addressable regions with an aqueous solution comprising a DNA molecule, the addressable regions being separated from each other by a space of at least 1 mm, and determining an amount of the at least one first labeling agent in each of the addressable regions.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications.

In some embodiments of any of the embodiments described herein, the method further comprises determining an amount of DNA in the addressable region.

In some embodiments of any of the embodiments described herein, determining an amount of DNA is effected by contacting the DNA with a second labeling agent (according to any of the respective embodiments described herein), optionally an intercalating agent.

In some embodiments of any of the embodiments described herein, determining an amount of DNA is effected subsequently to determining an amount of first labeling agent(s).

According to an aspect of some embodiments of the invention, there is provided an article of manufacture comprising a substrate, the substrate comprising a plurality of discrete regions separated by a hydrophobic region, each of the discrete regions comprising a positively charged substance, wherein in at least a portion of the discrete regions, a DNA molecule is attached to the positively charged substance, and the DNA molecule comprises at least one first labeling agent selective for an epigenetic DNA modification, and wherein a ratio of an amount of DNA in a discrete region to an area of the discrete region is in a range of from 1 ng/mm$^2$ to 150 ng/mm$^2$, optionally in a range of from 1 ng/mm$^2$ to 15 ng/mm$^2$, including any intermediate value and subrange therewithin.

In some embodiments of any of the embodiments described herein, the first labeling agent is a fluorescent labeling agent.

In some embodiments of any of the embodiments described herein, the substrate is a glass substrate.

In some embodiments of any of the embodiments described herein, an amount of DNA in each of at least a portion of the discrete regions is in a range of from 5 ng to 300 ng, optionally in a range of from 5 ng to 30 ng, including any intermediate value and subrange therewithin (e.g., according to any of the respective embodiments described herein).

In some embodiments of any of the embodiments described herein, an area of each of at least a portion of the discrete regions is in a range of from 1 mm$^2$ to 10 mm$^2$, including any intermediate value and subrange therewithin (e.g., according to any of the respective embodiments described herein).

In some embodiments of any of the embodiments described herein, the discrete regions are separated from one another by a space of at least 1 mm.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the DNA molecule comprises a plurality of first labeling agents, each of the plurality of first labeling agents being selective for a different type of epigenetic DNA modification.

In some embodiments of any of the embodiments described herein, the DNA molecule is further labeled by a second labeling agent (according to any of the respective embodiments described herein), optionally an intercalating agent.

In some embodiments of any of the embodiments described herein, the article of manufacture is for use in detecting an epigenetic DNA modification.

According to an aspect of some embodiments of the invention, there is provided a method of detecting an epigenetic DNA modification, the method comprising:
(a) attaching to a DNA molecule at least one first labeling agent (selective for a DNA modification);
(b) contacting an aqueous solution comprising the DNA molecule with at least one addressable region on a surface of a substrate, wherein the addressable region comprises a positively charged substance capable of attaching the DNA molecule to the surface, and the addressable region is surrounded by a hydrophobic region of the surface, and wherein a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$ (including any intermediate value and subrange therewithin);
(c) determining an amount of the at least one first labeling agent in the addressable region; and
(d) determining an amount of DNA in the addressable region.

In some embodiments of any of the embodiments described herein, the first labeling agent is a fluorescent labeling agent, and determining an amount of the labeling agent is effected by detecting fluorescence of the first labeling agent.

In some embodiments of any of the embodiments described herein, the method comprises cleaning the surface of the substrate subsequently to attaching the DNA molecule to the surface, and prior to determining an amount of the at least one first labeling agent.

In some embodiments of any of the embodiments described herein, cleaning is effected by rinsing with an aqueous liquid.

In some embodiments of any of the embodiments described herein, an amount of DNA in the aqueous solution contacted with the addressable region is in a range of from 5 ng to 300 ng, optionally in a range of from 5 ng to 30 ng, including any intermediate value and subrange therewithin (e.g., according to any of the respective embodiments described herein).

In some embodiments of any of the embodiments described herein, a concentration of DNA in the aqueous solution is in a range of from 5 ng/µl to 300 ng/µl, optionally in a range of from 5 ng/µl to 30 ng/µl, including any intermediate value and subrange therewithin (e.g., according to any of the respective embodiments described herein).

In some embodiments of any of the embodiments described herein, a ratio of an amount of DNA in the aqueous solution contacted with the addressable region to an area of the addressable region is in a range of from 1 ng/mm$^2$ to 150 ng/mm$^2$, optionally in a range of from 1 ng/mm$^2$ to 15 ng/mm$^2$, including any intermediate value and subrange therewithin (e.g., according to any of the respective embodiments described herein).

In some embodiments of any of the embodiments described herein, an area of the addressable region is in a range of from 1 mm$^2$ to 10 mm$^2$, including any intermediate value and subrange therewithin (e.g., according to any of the respective embodiments described herein).

In some embodiments of any of the embodiments described herein, the method comprises contacting a plurality of addressable regions with an aqueous solution comprising a DNA molecule, the addressable regions being separated from each other by a space of at least 1 mm, and determining an amount of the at least one first labeling agent in each of the addressable regions.

In some embodiments of any of the embodiments described herein, the positively charged substance comprises polylysine.

In some embodiments of any of the embodiments described herein, the epigenetic DNA modification is selected from the group consisting of a 5-methylcytosine residue, a 5-hydroxymethylcytosine residue, and DNA damage.

In some embodiments of any of the embodiments described herein, the method comprises attaching a plurality of first labeling agents to a DNA molecule, each of the plurality of first labeling agents being selective for a different type of epigenetic DNA modification, and determining an amount of each of the plurality of first labeling agents, thereby detecting a plurality of epigenetic DNA modifications.

In some embodiments of any of the embodiments described herein, determining an amount of DNA is effected by contacting the DNA with a second labeling agent (according to any of the respective embodiments described herein), optionally an intercalating agent.

In some embodiments of any of the embodiments described herein, determining an amount of DNA is effected subsequently to determining an amount of first labeling agent(s).

It is expected that during the life of a patent maturing from this application many relevant labeling agents will be developed and the scope of the term "labeling agent" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials

Deoxynucleotides (adenosine, guanosine and cytosine) were obtained from Sigma.

EvaGreen® dye (×2000 in DMSO) was obtained from Biotium.

Poly-L-lysine solution (0.1% in water) was obtained from Sigma.

PreCR® Repair Mix enzymatic cocktail was obtained from New England BioLabs.

T4 phage β-glucosyltransferase (BGT) was obtained from New England BioLabs.

UTP conjugated to ATTO-647 was obtained from Jena Bioscience.

Customized microscope slides with a PTFP/PTFE mask were obtained from Tekdon.

Familial Adenomatous Polyposis (FAP) Patient Selection and Treatment:

Male and female FAP patients at Tel Aviv Sourasky Medical Center who carry a nonsense stop-codon mutation in the APC gene were chosen. The patients were subjected to erythromycin treatment using the following protocol:

Pre-study evaluation included: ECG, Genetic evaluation for hereditary long QT syndrome and detailed family history. Baseline screening colonoscopy served as an inclusion for the study and by recording polyp count and measurement. The procedure was performed with a standardized forceps.

Study Period: Eligible carriers were given PO erythromycin 500×2 for 4 months with regular checkup including:
1. Weekly phone call from study coordinator for overall condition
2. ECG tests: after 3, 14, 60, 100 days for QT interval monitoring
3. Blood tests for CBC liver and kidney functions drawn at baseline, and after 2, 6, 10 and 15 weeks of treatment Endoscopic evaluation: endoscopies were conducted before (0-8 weeks pre-treatment) and after completing of erythromycin treatment (within 4 weeks). A single experienced endoscopist scored all polyps in the rectal stump/pouch/coon with written numeral estimation including size by dedicated standardized endoscopic forceps. Biopsies were taken from at least 2 locations from different polyps and normal colonic mucosa. Additionally, a video and multiple pictures were taken. In case of multiple polyps that cannot be counted multiple pictures were taken with recording of the largest polyp size and estimation of the "polyp carpet" dimensions.

Polyps in the duodenum were evaluated similarly.

Tissue samples were collected at −80° C. from both normal mucosa and colonic polyps. All endoscopies were performed by the experienced personnel of the high risk clinic at the Tel-Aviv Sourasky Medical Center.

Pathology analysis: All study samples were evaluated by an expert GI pathologist.

Mouse Glioblastoma Tumors and Normal Brain Tissues:

hGFAP-Cre, SynapsinI-Cre and C57BL/6 mice were obtained from Jackson Laboratories, and maintained within the Tel Aviv University SPF facility. Glioblastoma tumors were induced by lentivirus injection and orthotopic transplants. HRasV12-shp53 lentivirus was prepared and stereotaxically injected into the brains of transgenic mice, according to procedures described by Ikawa et al. [*Mol Ther* 2003, 8:666-673] and Friedmann-Morviski et al. [*Science* 2012, 338:1080-1084]. 005 tumor cells were stereotaxically injected into the brains of C57BL/6 wild-type mice ($3 \times 10^5$ per mouse), according to procedures described by Marumoto et al. [*Nat Med* 2009, 15:110-116]. Once mice had reached clinical end points, tumors were collected. Normal brain tissue was collected from healthy C57BL/6 wild-type mice.

Additional Tissue Samples:

4 and 7 healthy colon DNA samples and 3 and 6 sets of tumor and adjacent colon tissue of colorectal cancer patients were obtained from Amsbio and ReproCell, respectively.

Additional DNA samples from healthy colon, colon tumors and sets of tumor and adjacent colon tissue were obtained from OriGene.

Frozen peripheral blood mononuclear cells (PBMCs) of a multiple myeloma (MM) patient (male, aged 68, id. no. 14103813) and a chronic lymphocytic leukemia (CLL) patient (female, aged 76, id. no. 14103731) were obtained from HemaCare.

Healthy blood of a human donor (female, aged 31) was collected with informed consent for research use.

Mouse tissue from various organs was obtained according to procedures known in the art.

DNA Extraction:

Mouse tissue genomic DNA extraction: DNA was extracted from frozen (−80° C.) mouse tissues using an ArchivePure™ cell/tissue DNA purification kit (5 prime) according to manufacturer's instructions, with the following modifications: the frozen tissues were either immersed in liquid nitrogen and grounded to powder using a mortar and pestle, or diced on ice, immersed in lysis solution (5-prime) and homogenized using an electrical homogenizer. When liquid nitrogen was used, the powder of about 30-100 mg tissue was transferred to a 15 ml tube containing 3 ml of lysis solution and Proteinase K (Sigma) in a final concentration of 0.3-0.6 mg/ml. When electrical homogenization was used, only 20-30 mg of tissue was transferred to each tube. The tissues were digested overnight at 50° C. with shaking at 225 rpm. The next day, 15 µl RNase A solution (R6148, Sigma) was added and the tubes were mixed and incubated for 1 hour at 37° C. with 180 rpm shaking. Next, 1 ml of protein precipitation solution (5-prime) was added to the digested tissues, and the tubes were vortexed for 20 seconds and incubated on ice for 30 minutes. The tubes were then centrifuged at 7000×g for 30 minutes in a refrigerated centrifuge. The protein pellet was discarded and this step was repeated 3-4 additional times to guarantee protein-free DNA. The DNA was then precipitated with isopropanol and washed with 70% ethanol, and then hydrated with ultrapure water. DNA concentration was measured using a spectrophotometer.

Healthy blood DNA extraction: DNA was extracted from whole blood of a healthy individual using a GenElute™ mammalian genomic DNA Miniprep kit (Sigma) according to manufacturer's instructions.

Multiple myeloma (MM) and chronic lymphocytic leukemia (CLL) peripheral blood mononuclear cell (PBMC) DNA extraction: DNA was extracted from frozen peripheral blood mononuclear cells using a GenElute™ mammalian genomic DNA Miniprep kit (Sigma) according to manufacturer's instructions.

FAP patient normal mucosa and colonic polyp sample DNA extraction: Adenoma and healthy surrounding tissue samples were collected in liquid nitrogen. DNA was extracted using an AllPrep® DNA/RNA/protein kit (QIAGEN) according to manufacturer's instructions.

Pancreatic DNA extraction: Tissue samples were collected from both normal pancreatic tissue and pancreatic tumors, from male and female patients with pancreatic ductal adenocarcinoma (PDAC) at Tel Aviv Sourasky medical center. DNA was extracted using the Wizard® Genomic DNA Purification Kit (Promega), according to manufacturer's protocol for animal tissue, with the following minor alterations: tissue homogenization: 22-35 mg of each tissue were immersed in nuclei lysis solution and homogenized using and electrical homogenizer. Protein precipitation: 1 ml protein precipitation solution (5-prime) was added to the lysate, in addition to 200 µl protein precipitation solution (Promega). Centrifugation: all centrifugation steps were performed at 7000×g.

5-Hydroxynethylcytosine (5-hmC) Labeling and Cleaning:

5-hmC was fluorescently labeled via a two-step chemoenzymatic reaction, according to procedures described in Shahal et al. [*Anal Chem* 2014, 86:8231-8237], Gilat et al. [*Clin Epigenet* 2017, 9:70], and Michaeli et al. [*Chem Commun (Camb)* 2013, 49:8599-8601]. In each reaction tube, 1 µg of genomic DNA was mixed with 3 µl of 10× buffer 4 (New England Biolabs), UDP-6-N3-Glu (prepared according to procedures described in Nifker et al. [*ChemBioChem* 2015, 16:1857-1860]) to a final concentration of 45 µM, 2 µl (20 units) of T-4 β-glucosyltransferase (New England Biolabs), and ultrapure water to a final volume of 30 µl. The reaction mixture was incubated overnight at 37° C. The number of reaction tubes varied according to experiments' requirements and was usually two. The following day, dibenzocyclooctyl (DBCO)-PEG$_4$-5/6-TAMRA (Jena Bioscience) was added to a final concentration of 150 µM and the reaction was incubated overnight at 37° C. The labeled DNA samples were purified from excess fluorophores using Oligo Clean & Concentrator™ columns (Zymo Research), according to manufacturer's recommendations, with 3 washing steps for optimal results. For best yield, only up to two micrograms of DNA (two reaction tubes) were loaded on one column. Alternatively, samples were cleaned with isopropanol/ethanol DNA precipitation, but the result was not as clean. Samples were kept at 4° C. until analyzed.

Control samples for 5-hmC labeling were identical to other samples, except that the (3-glucosyltransferase enzyme was omitted from their tubes. The result is a non-labeled DNA sample with fluorescence signal that derives only from fluorescent dye molecules not specifically attached to 5-hmC residues, representing the assay's noise level (the baseline fluorescent signal in the absence of 5-hmC residues). This signal can be subtracted during analysis to retain the signal deriving only from labeled 5-hmC residues.

Total DNA Staining:

The total DNA was stained with EvaGreen® DNA binding dye (Biotium). 1 µl of 1.25 µM dye (in 90% water, 10% DMSO) was added to the wells containing the bound DNA. Slides were covered to avoid light exposure and incubated for 30 minutes at room temperature. The slides were then washed with water and dried with N2 gas. Wells containing only water and no DNA were also stained, in order to obtain the background signal of the dye when not bound to DNA.

Slide Imaging:

Slides were imaged using an FLA-5100™ (Fujifilm) or InnoScan™ 1100 AL (Innopsys) fluorescent imaging device. Excitation laser beam used to image the TAMRA fluorophore was at a wavelength of 532 nm (with a 575 nm long-pass filter in the FLA-5100™ device and a 582/75 nm filter in the InnoScan™ device). Excitation laser beam used to image the EvaGreen® fluorophore was at a wavelength of 473/488 nm (with a 510 nm long-pass filter in the FLA-5100™ device and a 520/5 nm filter in the InnoScan™ device). Since the two fluorophores overlap in part of their spectrum, the TAMRA fluorophore was imaged only in the absence of the EvaGreen® dye. Only after the TAMRA imaging, the total DNA was stained and then imaged using the EvaGreen® dye channel. Some FRET (Forster resonance energy transfer) occurred between EvaGreen® dye and TAMRA during EvaGreen® dye imaging; however, since the 5-hmC level in DNA samples observed was less than 0.1%, the loss of total DNA signal due to FRET was considered to be negligible. Scanning parameters were optimized to fit the entire range of fluorescence intensities on the scanned slides and to avoid technical artifacts such as saturation and photomultiplier non-linearity.

HPLC-Mass Spectrometry:

5-hmC level in selected samples was assessed using LC-MS/MS (liquid chromatography-tandem mass spectroscopy). In order to quantify 5-hmC using this technique, a calibration curve was prepared. The calibration curve was built from synthetic DNA fragments with known 5-hmC levels. A linear fit was plotted, and the 5-hmC level of a given sample was interpolated. The 5-hmC residues in the samples and calibration standards were converted to 6-azide-β-glucosyl-5-hydroxymethylcytosine (N3-5-gmC) in order to significantly increase the LC-MS/MS sensitivity to 5-hmC. Otherwise, 5-hmC suffers from relatively low ionization efficiency and possible ion suppression from co-eluted cytosine.

In order to prepare calibration standards, two kinds of 1052 base pair long DNA fragments were amplified by PCR from a Lambda DNA template. One fragment contained two 5-hmC residues, and the other contained none. By mixing the two products in several ratios, a range of 0-0.0951% 5-hmC of total nucleotides was obtained. To create the fragment with two 5-hmC residues, we used forward and reversed primers that contained one internal 5-hmC each. Similar primers with cytosine instead of 5-hmC were used to create the fragment with no 5-hmC. A typical reaction was performed in a volume of 50 µl containing 200 ng of template DNA, 0.4 µM of the primers, and one unit myTaq™ PCR mix (Bioline). Final volume was completed with ultrapure water. PCR (Eppendorf MC Pro gradient S) was conducted according to the following protocol: incubation at 95° C. for 30 sec as an initial step, followed by 30 cycles of 30 seconds at 95° C., 60 seconds at 53° C., and 90 seconds at 68° C., and finally 10 minutes at 68° C. The PCR products were cleaned of free nucleotides and primers using the Qiaquick® PCR purification kit (Qiagen). The length of DNA fragments was confirmed by gel electrophoresis at 100 V for 45 minutes on 1% agarose gel pre-stained with SYBR® Safe gel stain (ThermoFisher).

5-hmC was converted to N3-5-gmC by mixing 2 μg of genomic DNA with 3 μl of (10×) buffer 4 (New England BioLabs), UDP-6-N3-Glu (prepared as described herein) to a final concentration of 100 μM, 2 μl (20 units) of T4-BGT (New England BioLabs), and ultrapure water to a final volume of 30 μl. The reaction mixture was incubated overnight at 37° C.

Genomic and synthetic DNA samples were enzymatically hydrolyzed using DNA Degradase Plus™ nuclease mix (Zymo Research), which degrades DNA to individual nucleosides. 3.9 μl of (10×) DNA Degradase™ Reaction Buffer (Zymo Research) and 2 μl of enzyme were added to the DNA tube after the 5-hmC conversion to N3-5-gmC. The reaction mixture was incubated at 37° C. for two hours. Enzyme inactivation was performed at 70° C. for 20 minutes. The resulting nucleoside mixture was filtered by an Amicon® Ultra (0.5 ml 10K) preconditioned column (Merck). The eluted solution was then applied to a glass vial with an insert, and 10 μL of filtered sample were injected into the LC-MS/MS system.

LC-MS/MS system, conditions, and analysis: The chromatographic separations were performed on an Acquity UPLC® system (Waters) using an Xselect™ HSS T3 column (2.5 μm, 2.1×75 mm, Waters), which was maintained at 40° C. The mobile phase consisted of 0.1% formic acid in water (solvent A) and 0.1% formic acid in acetonitrile (solvent B). Nucleosides were eluted at a flow rate of 0.3 ml/minute with a gradient of 100% solvent A from minute 0 to 1, then a linear increase to 4.0% solvent B from minute 1 to 2, to 9.0% solvent B from minute 2 to 4 and to 20.0% solvent B from minute 4 to 5. Mobile phase was maintained at 20% solvent B for additional 30 seconds (minute 5 to 5.5). The composition was then returned to the initial conditions and held under these elution conditions until minute 8. The effluent from the column was directed into an electrospray ion source and then streamed into a Xevo® TQD triple quadrupole mass spectrometer (Waters). The measurements of targeted nucleosides were conducted in a positive ion mode by multiple reaction monitoring (MRM) with the following transitions (dN refers to the different nucleosides): dC m/z 228→112, 250→134, dT m/z 243→117, 127, dA m/z 252→136, 119, dG m/z 268→135, 152, 5-hmdC m/z 258→124, 142, 5-mdC m/z 242→126, 264→148, 5-gmdC m/z 421→269, N3-5-gmdC m/z 445→124, 329. The MRM parameters (e.g., cone and collision cell voltage) of each nucleoside were automatically optimized to achieve maximal detection sensitivity. Each sample was measured twice.

5-hmC level calculation: The relative content of 5-hmC (present as N3-5-gmdC) in each sample was calculated from the MRM peak area of this species, divided by the sum of peak areas of all other nucleosides. A calibration curve of 5 points was created with the peak areas of the calibration standards, and the absolute 5-hmC value of the genomic samples was interpolated.

Data Analysis:

Images obtained from the FLA-5100™ fluorescent image analyzer were converted to 16-bit gray TIFF files that keep original image resolution using Image Gauge™ software (Fujifilm). These TIFF images and the TIFF images generated by the InnoScan™ 1100 AL device were analyzed using ImageJ software according to procedures described in Schneider et al. [*Nature Methods* 2012, 9:671-675]. Each well was identified manually or using a script, and the mean fluorescence intensity inside each well in both channels was extracted.

The mean TAMRA fluorescence intensity of a sample's control was subtracted from the mean TAMRA fluorescence intensity of the labeled sample, to obtain the fluorescence only deriving from fluorescent molecules attached to 5-hmC residues. This subtracted signal was divided by the total DNA mean fluorescence (n channel) as determined by EvaGreen® dye signal after background subtraction, in order to normalize the signal according to the actual amount of DNA attached to the well. The average and standard deviation of 4-5 replicates are then calculated, and the resulting average value is the relative 5-hmC signal of the sample in the experiment. The absolute 5-hmC level was attained by comparing the result to the results obtained for calibration samples with known 5-hmC level, as follows:

$$\% \frac{5\text{-}hmC}{\text{total nucleobasess}} = \text{sample's relative } 5\text{-}hmC \text{ value (exp.)} * \frac{\text{calibration sample's known } 5\text{-}hmC \text{ level } (LC-MS/MS)}{\text{calibration sample's relative } 5\text{-}hmC \text{ value (exp.)}}$$

wherein:

$$\text{relative } 5\text{-}hmC \text{ value (exp.)} = \frac{\sum_{1}^{n} \frac{TAMRA \text{ fluorescence signal}}{\text{(well with labeled sample} - \text{mean of control)}}}{\text{EvaGreen fluorescence signal}} \frac{\text{(well of labeled sample} -}{\text{EvaGreen background noise)}}}{n}$$

Statistical Analysis:

Student's t-test was used to evaluate statistical significance of the differences between the healthy samples and the colon and glioblastoma tumors.

Example 1

Substrate with Positively Charged Wells

Regular microscope slides (Thermo Scientific) were cleaned by overnight immersion in acid (a 2:1 mixture of nitric acid: hydrochloric acid) at room temperature. The slides were then carefully washed with water before being immersed in an aqueous poly-L-lysine solution (0.005 weight percent). A mask with a multi-well pattern was prepared by perforating an adhesive ThermalSeal® RT™ sealing film (Sigma) with 1.8 mm holes using an infrared laser. The perforated film was then taped to a dry glass slide shortly prior to use.

Alternatively, microscope slides with a customized pattern (depicted in FIG. 1) of 2.0 mm diameter wells and PTFP/PTFE mask with a 20-30 μm thickness were immersed in an aqueous poly-L-lysine solution (0.005 weight percent, prepared from a 0.1% aqueous poly-L-lysine solution, in order to positively charge the portions of surface not covered by the hydrophobic mask. The immersed slides were incubated for one hour at 37° C. with light shaking (25 rpm) and then overnight at 4° C. (no shaking). The following day a blocking step was performed. The slides were washed twice with PBST solution (phosphate buffer saline (PBS)

with 0.05% Tween™-20 detergent) and twice with PBS (Sigma), and immersed in a 5% (w/v) bovine serum albumin (Sigma) solution in PBS. The immersed slides were incubated for one hour at 37° C. with light shaking (25 rpm) and then overnight at 4° C. (no shaking). In the concluding step, the slides were washed 3 times with PBS and then 3 times with Milli-Q™ purified water and dried with N2 gas. The slides were used immediately upon drying.

Example 2

Determination of 5-Hydroxymethylcytosine (5-hmC) Levels

In order to immobilize DNA onto wells of slides prepared as described hereinabove, 1 µl samples were placed in each well of slides prepared according to procedures described in Example 1. The optimal DNA concentration for attachment is 5-30 ng; however 15-300 ng were used. The slides contained 4-5 replicates of each sample. The slides were incubated for 14 minutes at 42° C. and then for 24 minutes at 30° C., under humid conditions in order to avoid rapid drying of the wells. The slides were then washed with water and dried with N2 gas, and kept in the dark.

Figures 2A, 2B, 2C, 2D:
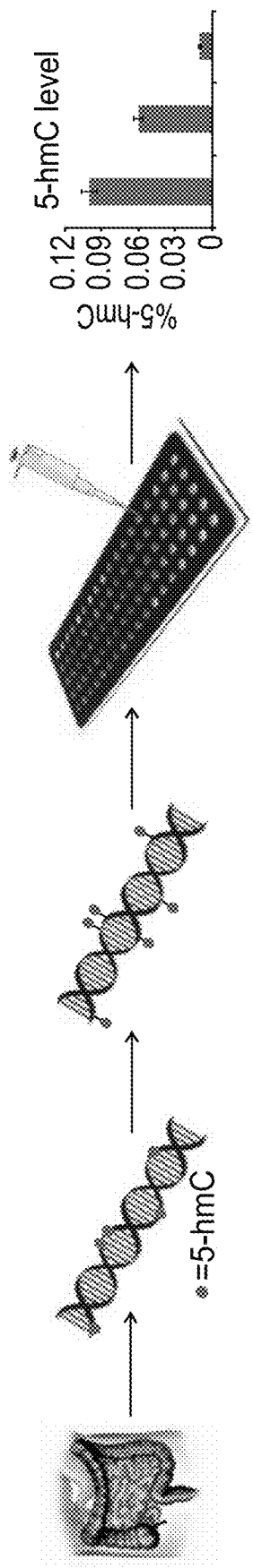
FIGS. 2A-2D present a schematic illustration of an assay workflow according to some embodiments of the invention, showing extraction of DNA (comprising 5-hmC residues) from a specimen (FIG. 2A), fluorescent labeling of 5-hydroxymethylcytosine (5-hmC) residues in DNA samples using a chemoenzymatic reaction (FIG. 2B), electrostatically binding the DNA to a surface of a multi-well poly-L-lysine-coated glass substrate and fluorescent imaging of the substrate (FIG. 2C), and determination of 5-hmC levels by data analysis (FIG. 2D).
Figure 3A:
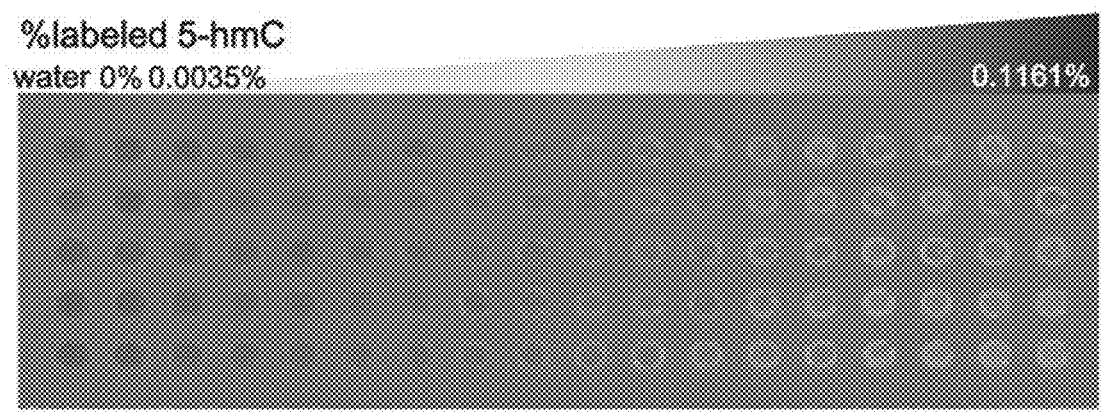
FIGS. 3A-3E shows a validation experiment for an assay according to some embodiments of the invention, wherein 25 ng of DNA of various ratios of a labeled sample and a control sample, providing various percentages of labeled 5-hmC, were placed in each column of a glass slide array, wherein the sample's 5-hmC level was determined by HPLC-MS to be 0.1161% of total nucleotides, and the percentage of labeled 5-hmC in each column of 5 wells (ranging from 0.0035% to 0.1161%) was calculated according to the dilution factor.
Figure 3B:
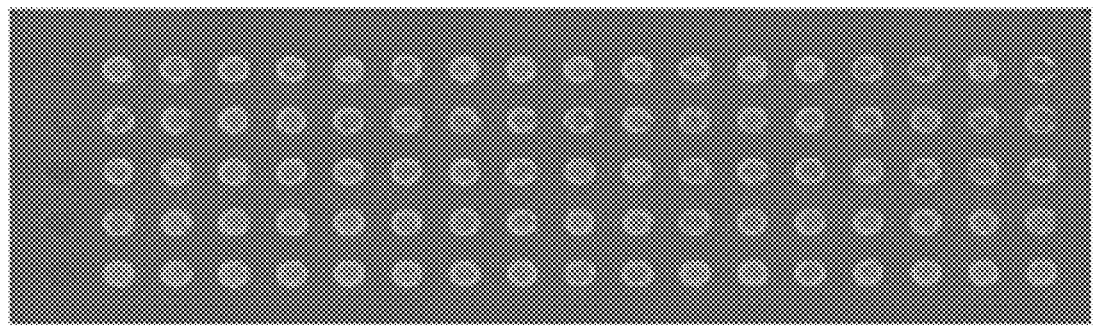
Figure 3C:
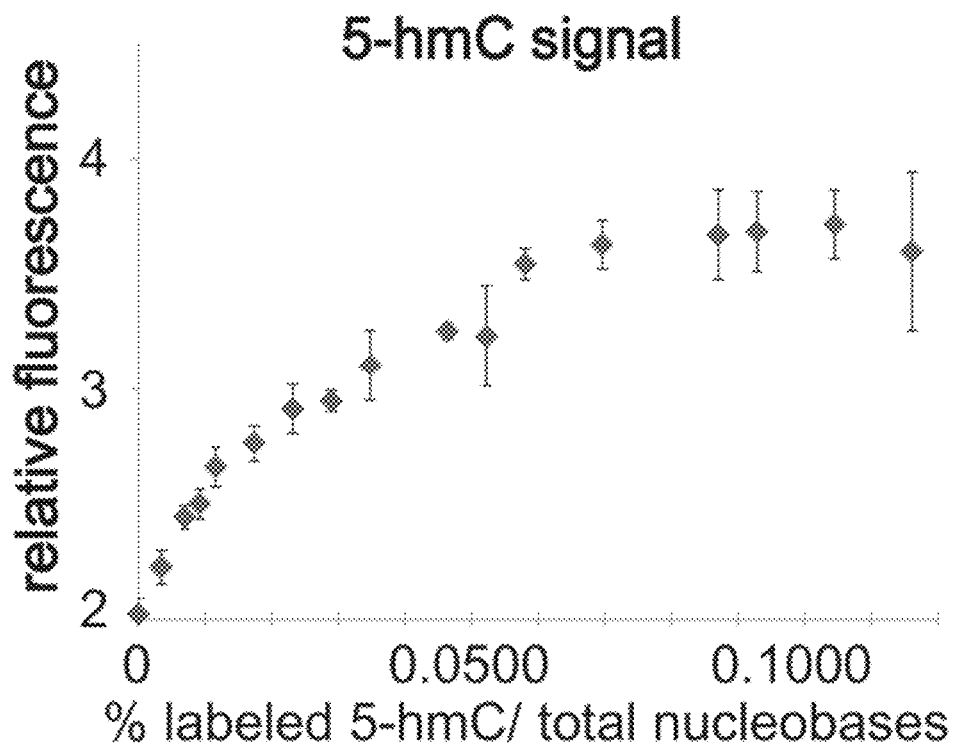
Figure 3D:
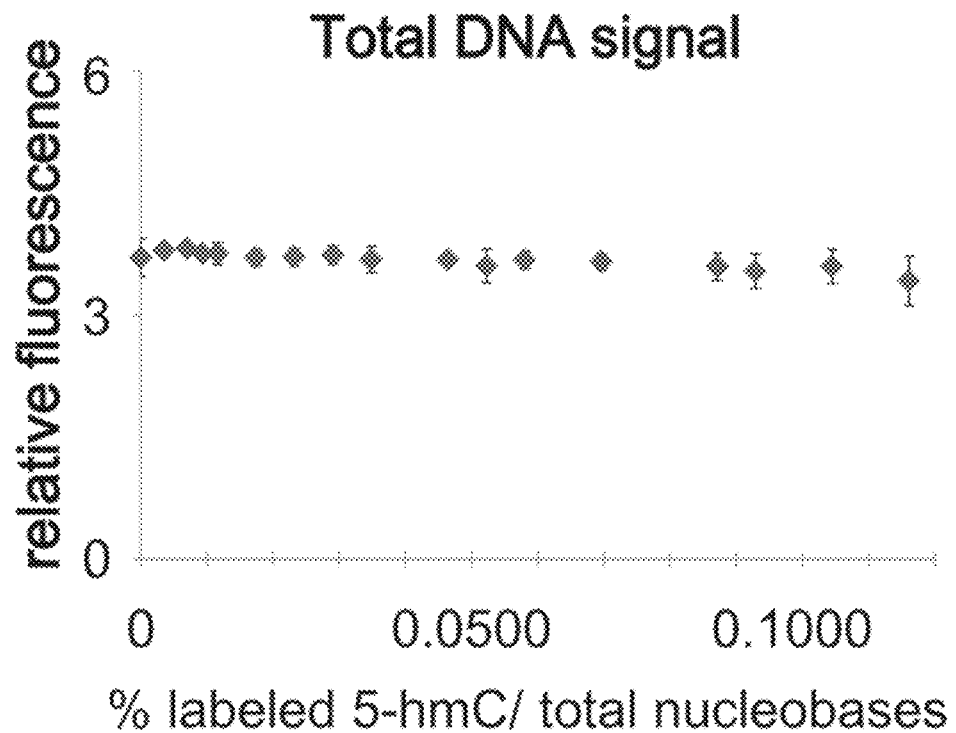
Figure 3E:
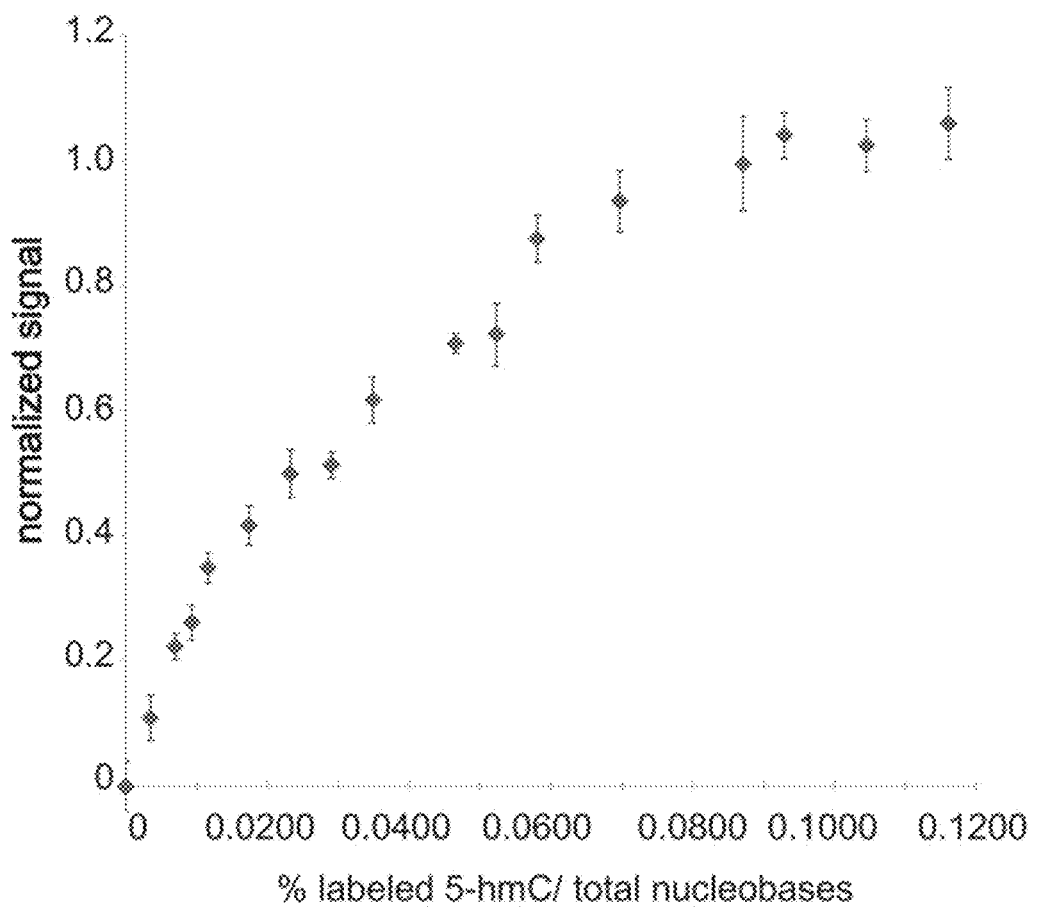

The protocol used for determining 5-hmC levels is depicted in FIGS. 2A-2D. The 5-hmC residues in genomic DNA samples (FIG. 2A) were fluorescently labeled via a chemoenzymatic reaction (according to procedures described in the Materials and Methods section hereinabove) and the samples were then purified from residual fluorophores (FIG. 2B). The cleaning step is important since unbound fluorophores can nonspecifically bind to the surface and create high noise level. The resulting labeled DNA samples were electrostatically bound to the surface of a multi-well poly-L-lysine-coated glass slide as described hereinabove, and the slide was then imaged via a fluorescence imager (FIG. 2C), and the relative 5-hmC level was determined from data analysis (FIG. 2D), according to procedures described in the Materials and Methods section hereinabove.

In order to confirm reproducibility of the assay, a DNA sample was independently labeled four times and five replicates for each of the aforementioned four samples was applied on a slide. The assay results were clearly reproducible, with the four equivalent samples exhibiting (non-calibrated, normalized) signals of $0.1331\pm0.0218$, $0.1235\pm0.0149$, $0.1451\pm0.0228$, and $0.1372\pm0.0119$.

In order to validate the assay and assess its sensitivity, a DNA sample with fluorescently labeled 5-hmC residues was diluted with a control sample (according to procedures described in the Materials and Methods section hereinabove) in several ratios, from 100% labeled sample and 0% control to 0% labeled sample and 100% control, and the mixed samples were detected on a slide. The final amount of DNA was kept constant: 25 ng per well. The sample's 5-hmC level was determined by HPLC-MS to be 0.1161% and the percentages of labeled 5-hmC in the diluted samples were calculated according to the dilution factor.

As shown in FIGS. 3A-3E, the activated surface successfully bound DNA, and the signal of the total DNA was relatively steady along replicates of the same sample and along different samples with 25 ng. As further shown therein, the fluorescence signal of the 5-hmC residues increased with the rise in labeled 5-hmC percentage, and the noise level, represented by the fluorescence intensity of the control sample, was very low, and the difference between the control sample and 0.003% labeled 5-hmC was significant.

These results indicate the assay's ability to detect very low 5-hmC levels, lower than the level reported in blood [Gilat et al., Clin Epigenet 2017, 9:70]. The dilution also enabled the determination of the linear range of the fluorescence as a function of the amount of fluorophores per well, and the derivation of a function that properly represents this relationship for every amount of fluorophore.

In order to further validate the assay, the 5-hmC level was determined in various mouse tissues to reaffirm the tissue-specific nature of 5-hmC distribution reported previously.

Figure 4A:
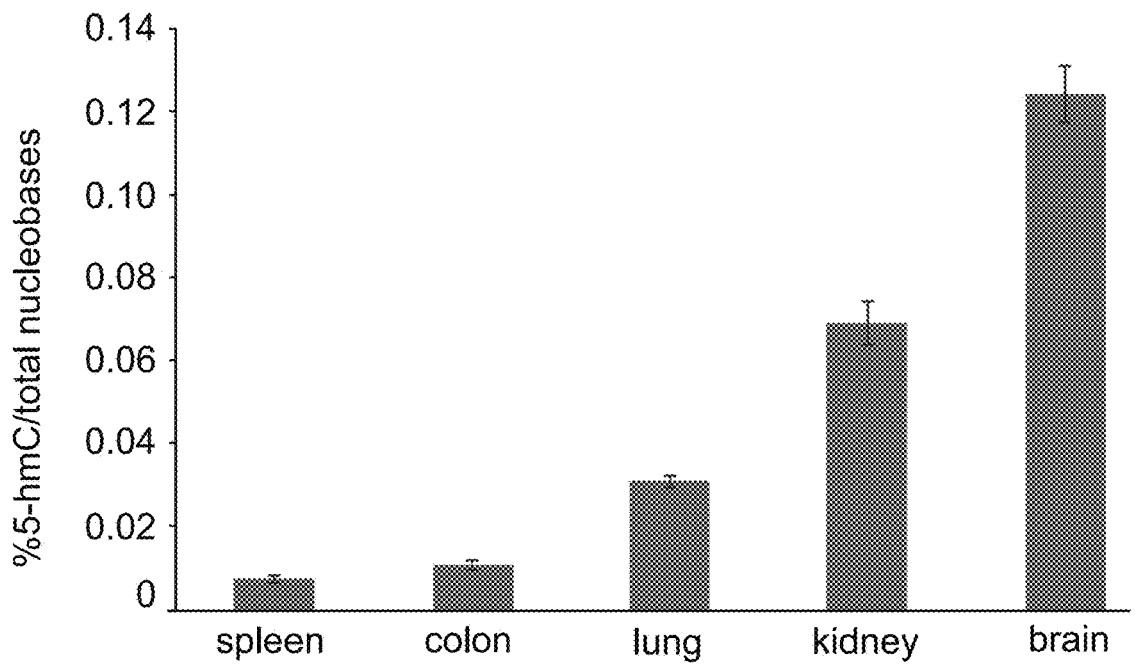
FIGS. 4A and 4B presents a bar graph (FIG. 4A) showing 5-hmC level in several mouse tissues as determined according to an exemplary assay (calibrated with LC-MS/MS) (error bars represent standard deviation of 4-5 replicates), and a graph (FIG. 4B) showing 5-hmC level of the same samples as determined by LC-MS/MS as a function of optical signal according to an exemplary assay (error bars in x-axis represent standard deviation of 4-5 replicates in optical measurements, and error bars in y-axis represent standard deviation of two LC-MS/MS runs.

As shown in FIG. 4A, the 5-hmC level detected in mouse brain was $0.1242\pm0.0068\%$ of total nucleobases, $0.0690\pm0.0053\%$ in mouse kidney, $0.0308\pm0.0013\%$ in mouse lung, $0.0107\pm0.0010\%$ in mouse colon, and $0.0074\pm0.0007\%$ in mouse spleen.

The above results are consistent with levels reported in the literature, in which the central nervous system contains the highest levels of 5-hmC, an intermediate level is present in kidneys and lungs, and a lower level is found in colon and spleen [Bachman et al., Nat Chem 2014, 6:1049-1055; Globisch et al., PLoS One 2010, 5:e15367; Shahal et al., Anal Chem 2014, 86:8231-8237].

Figure 4B:
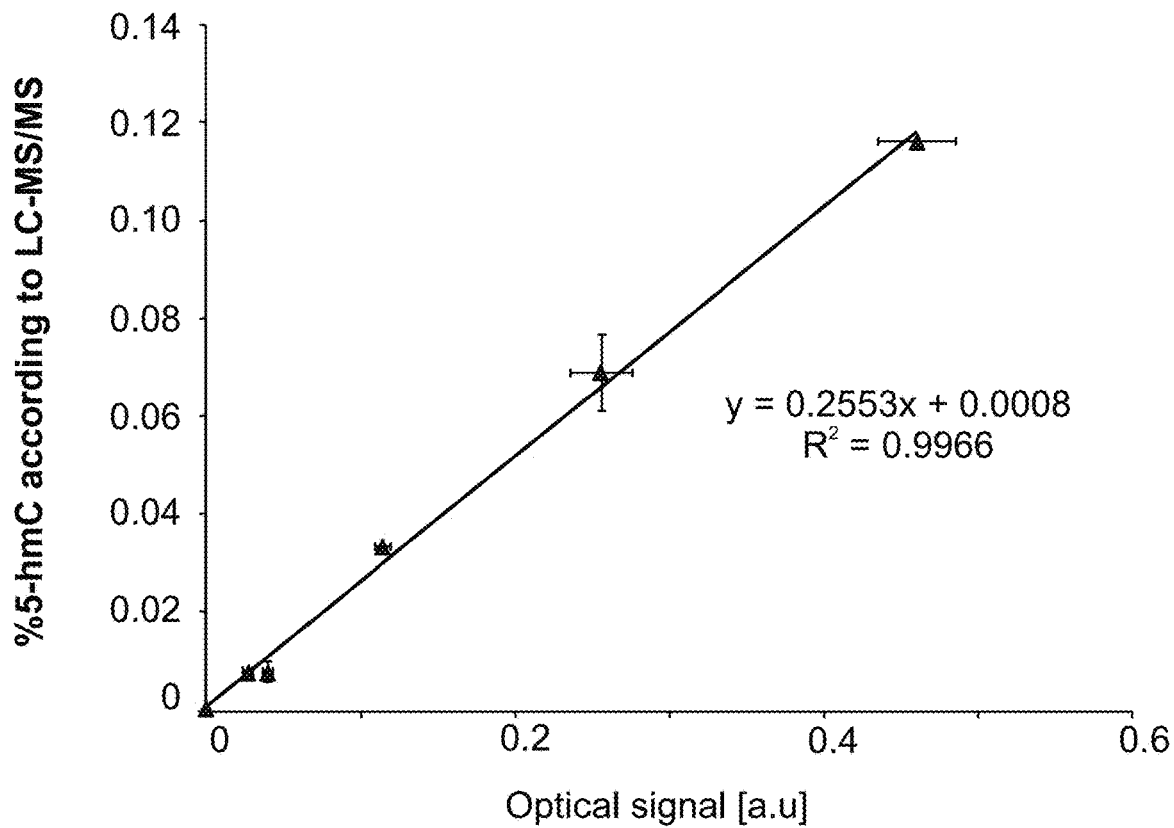

As shown in FIG. 4B, the optical signal obtained from various tissues according to the assay described herein was strongly and linearly correlated to the results of LC-MS/MS analysis.

These results confirm that the assay is applicable over a wide range of 5-hmC levels, and that LC-MS/MS calibration is appropriate.

Example 3

Determination of 5-Hydroxymethylcytosine (5-hmC) Levels in Cancerous Tissue

In order to assess the ability of a multi-array assay such as described herein described in Example 2 to detect cancer, the 5-hmC levels of various tissue types (from sources as described in the Materials and Methods section) were determined according to procedures described in Example 2.

The results of individual samples are presented in Table 1 below, and summarized in FIGS. 5A and 5B.

Figure 5A:
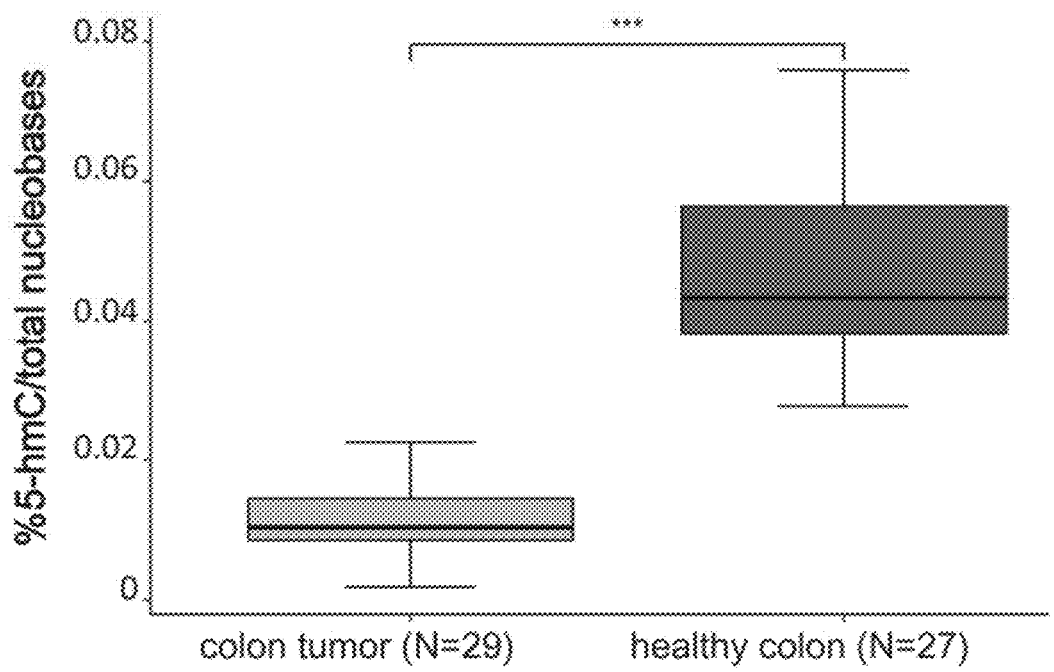
FIGS. 5A and 5B present a boxplot representation (FIG. 5A) showing 5-hmC levels (as a percentage of total nucleobases) in healthy colon samples (N=27) and in colon tumors (N=29) (boxes correspond to 25-75 percentiles, line within box indicates median, whiskers indicate 1.5 times the inter-quartile range, *** p<0.001); and a circular bar plot (FIG. 5B) showing 5-hmC levels in colon tumor and adjacent tissue sets (matched) from 25 patients (tumor and match error bars indicate standard deviation of 3-5 replicates), compared to 5-hmC levels in healthy tissue (N=27) indicated by surrounding circle.

As shown in FIG. 5A, a significant reduction ($p<0.001$) in 5-hmC level was observed for colon tumors ($0.0133\pm0.0096\%$, N=29) compared with healthy colon tissue ($0.04709\pm0.0133\%$, N=27).

Figure 5B:
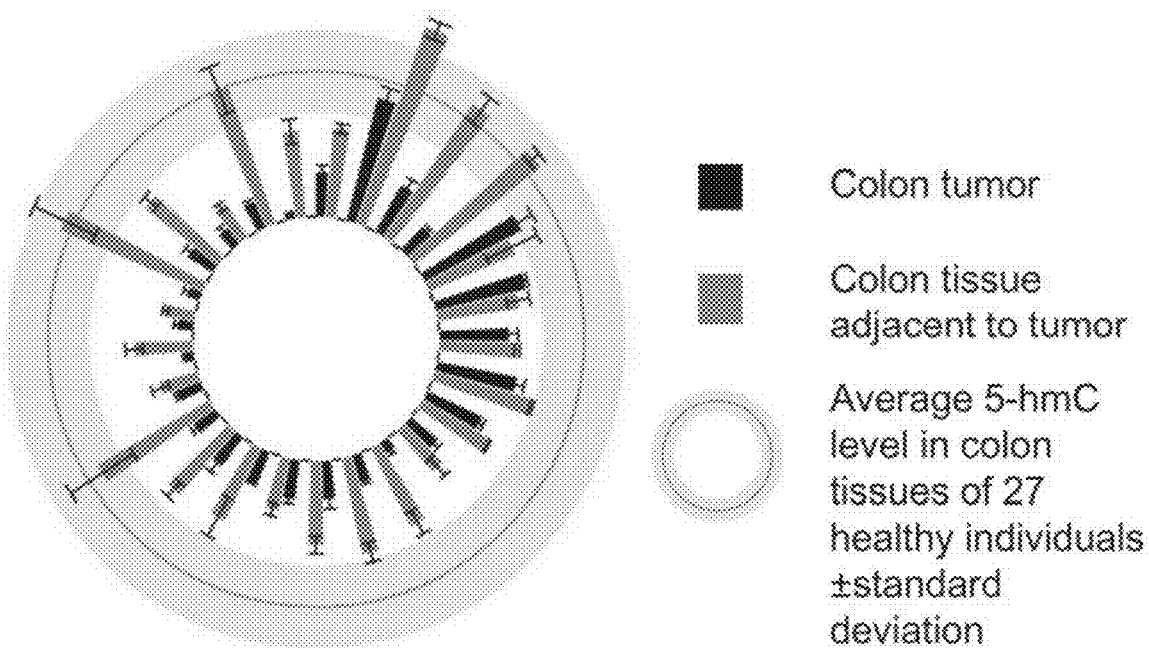

As shown in FIG. 5B, the 5-hmC levels of colon tissues adjacent to tumors of colorectal cancer patients (matched tissues) were either higher than or identical to the 5-hmC levels of their neighboring tumor, with considerable variability. In some of the cases the 5-hmC level of tissue adjacent to a tumor was very high, close to the healthy samples average 5-hmC level or higher, and in other cases it was lower and close to the tumor 5-hmC level. Despite high variability between individuals, in most cases the adjacent tissue exhibits some reduction of 5-hmC levels relative to healthy tissue.

These results suggest that quantification of tissue 5-hmC can be used to diagnose cancer, and/or to assess health of tissue to adjacent to a tumor (which is not usually pathologically evaluated), which may optionally impact treatment strategy and/or assist in disease staging.

These results are also in line with reports that the gene expression profile of tissue adjacent to tumors may indicate an intermediate stage, between healthy and tumorous [Aran et al., Nat Commun 2017, 8:1077].

The 5-hmC level was also determined in pancreatic tumors and matched tissue from the tumor periphery of four pancreatic ductal adenocarcinoma (PDAC) patients; as well as from polyps and adjacent tissues in two monitored familial adenomatous polyposis (FAP) patients, before and after antibiotic read-through treatment for their APC non-sense mutations [Gupta & DuBois, Nat Rev Cancer 2001, 1:11-21; Cruz-Correa et al., Gastroenterology 2002, 122: 641-6451.

TABLE 1

5-hmC levels (% of total nucleotides and standard deviation) in individual samples of colon tumor, tissue adjacent to colon tumors, and healthy colon tissue

| Sample type | Gender | Age | Cancer stage | % 5-hmC | Standard deviation |
|---|---|---|---|---|---|
| colon tumor | Male | 72 | IV | 0.0198 | 0.0013 |
| tissue adjacent to colon tumor | | | | 0.0256 | 0.0003 |
| colon tumor | Male | 85 | I | 0.0226 | 0.0030 |
| tissue adjacent to colon tumor | | | | 0.0253 | 0.0009 |
| colon tumor | Male | 64 | IIA | 0.0265 | 0.0027 |
| tissue adjacent to colon tumor | | | | 0.0333 | 0.0005 |
| colon tumor | Male | 45 | II | 0.0303 | 0.0009 |
| tissue adjacent to colon tumor | | | | 0.0268 | 0.0038 |
| colon tumor | Male | 45 | II | 0.0145 | 0.0021 |
| tissue adjacent to colon tumor | | | | 0.0289 | 0.0015 |
| colon tumor | Male | 79 | III C2 | 0.0410 | 0.0040 |
| tissue adjacent to colon tumor | | | | 0.0676 | 0.0029 |
| colon tumor | Female | 76 | III | 0.0174 | 0.0031 |
| tissue adjacent to colon tumor | | | | 0.0518 | 0.0049 |
| colon tumor | Male | 69 | III C2 | 0.0356 | 0.0054 |
| tissue adjacent to colon tumor | | | | 0.0303 | 0.0091 |
| colon tumor | Female | 76 | III | 0.0105 | 0.0011 |
| tissue adjacent to colon tumor | | | | 0.0520 | 0.0022 |
| colon tumor | Female | 71 | IIIA | 0.0115 | 0.0017 |
| tissue adjacent to colon tumor | | | | 0.0174 | 0.0036 |
| colon tumor | Female | 65 | IV | 0.0092 | 0.0015 |
| colon tumor | Female | 60 | IIIC | 0.0085 | 0.0010 |
| colon tumor | Female | 55 | IIIC | 0.0106 | 0.0017 |
| colon tumor | Female | 42 | IIIB | 0.0040 | 0.0011 |
| tissue adjacent to colon tumor | | | | 0.0281 | 0.0042 |
| colon tumor | Male | 53 | IIIB | 0.0093 | 0.0008 |
| tissue adjacent to colon tumor | | | | 0.0316 | 0.0033 |
| colon tumor | Male | 38 | IIIC | 0.0124 | 0.0031 |
| tissue adjacent to colon tumor | | | | 0.0270 | 0.0028 |
| colon tumor | Male | 53 | IV | 0.0093 | 0.0004 |
| colon tumor | Male | 59 | IIIC | 0.0129 | 0.0014 |
| tissue adjacent to colon tumor | | | | 0.0173 | 0.0021 |
| colon tumor | Male | 70 | IIIB | 0.0113 | 0.0005 |
| tissue adjacent to colon tumor | | | | 0.0261 | 0.0070 |
| colon tumor | Female | 67 | IV | 0.0117 | 0.0035 |
| tissue adjacent to colon tumor | | | | 0.0274 | 0.0030 |
| colon tumor | Female | 66 | IIIC | 0.0086 | 0.0015 |
| tissue adjacent to colon tumor | | | | 0.0422 | 0.0121 |
| colon tumor | Female | 53 | IIA | 0.0087 | 0.0008 |
| tissue adjacent to colon tumor | | | | 0.0130 | 0.0030 |
| colon tumor | Male | 75 | IIB | 0.0031 | 0.0005 |
| tissue adjacent to colon tumor | | | | 0.0192 | 0.0029 |
| colon tumor | Male | 84 | IIA | 0.0052 | 0.0013 |
| tissue adjacent to colon tumor | | | | 0.0098 | 0.0009 |
| colon tumor | Male | 64 | IIA | 0.0043 | 0.0015 |
| tissue adjacent to colon tumor | | | | 0.0504 | 0.0110 |
| colon tumor | Male | 61 | | 0.0098 | 0.0019 |
| tissue adjacent to colon tumor | | | | 0.0300 | 0.0026 |
| colon tumor | Male | 75 | IIA | 0.0062 | 0.0018 |
| tissue adjacent to colon tumor | | | | 0.0129 | 0.0014 |
| colon tumor | Male | 60 | IIA | 0.0093 | 0.0011 |
| tissue adjacent to colon tumor | | | | 0.0469 | 0.0081 |
| colon tumor | Female | 76 | IIA | 0.0019 | 0.0004 |
| tissue adjacent to colon tumor | | | | 0.0279 | 0.0041 |
| healthy colon | Female | 36 | — | 0.0462 | 0.0005 |
| healthy colon | Male | 55 | — | 0.0564 | 0.0012 |
| healthy colon | Female | b. 1950 | — | 0.0565 | 0.0015 |
| healthy colon | Male | 23 | — | 0.0371 | 0.0037 |
| healthy colon | Female | 56 | — | 0.0410 | 0.0031 |
| healthy colon | Female | 65 | — | 0.0483 | 0.0019 |
| healthy colon | Female | 30 | — | 0.0395 | 0.0012 |
| healthy colon | Male | 65 | — | 0.0242 | 0.0020 |
| healthy colon | Male | 75 | — | 0.0306 | 0.0012 |
| healthy colon | Male | 78 | — | 0.0318 | 0.0028 |
| healthy colon | Male | 74 | — | 0.0314 | 0.0063 |
| healthy colon | Female | 66 | — | 0.0371 | 0.0048 |
| healthy colon | Female | 62 | — | 0.0759 | 0.0076 |
| healthy colon | Male | 74 | — | 0.0444 | 0.0025 |
| healthy colon | Female | 68 | — | 0.0507 | 0.0035 |
| healthy colon | Female | 70 | — | 0.0607 | 0.0049 |
| healthy colon | Female | 69 | — | 0.0603 | 0.0046 |
| healthy colon | Male | 66 | — | 0.0652 | 0.0141 |
| healthy colon | Female | 67 | — | 0.0433 | 0.0006 |
| healthy colon | Male | 64 | — | 0.0668 | 0.0144 |
| healthy colon | Male | 64 | — | 0.0753 | 0.0087 |
| healthy colon | Male | 61 | — | 0.0415 | 0.0079 |
| healthy colon | Male | 60 | — | 0.0401 | 0.0084 |
| healthy colon | Female | 66 | — | 0.0456 | 0.0098 |
| healthy colon | Male | 73 | — | 0.0418 | 0.0067 |
| healthy colon | Female | 76 | — | 0.0395 | 0.0102 |
| healthy colon | Male | 80 | — | 0.0277 | 0.0083 |
| healthy colon | Male | 78 | — | 0.0369 | 0.0083 |

Figure 6A:
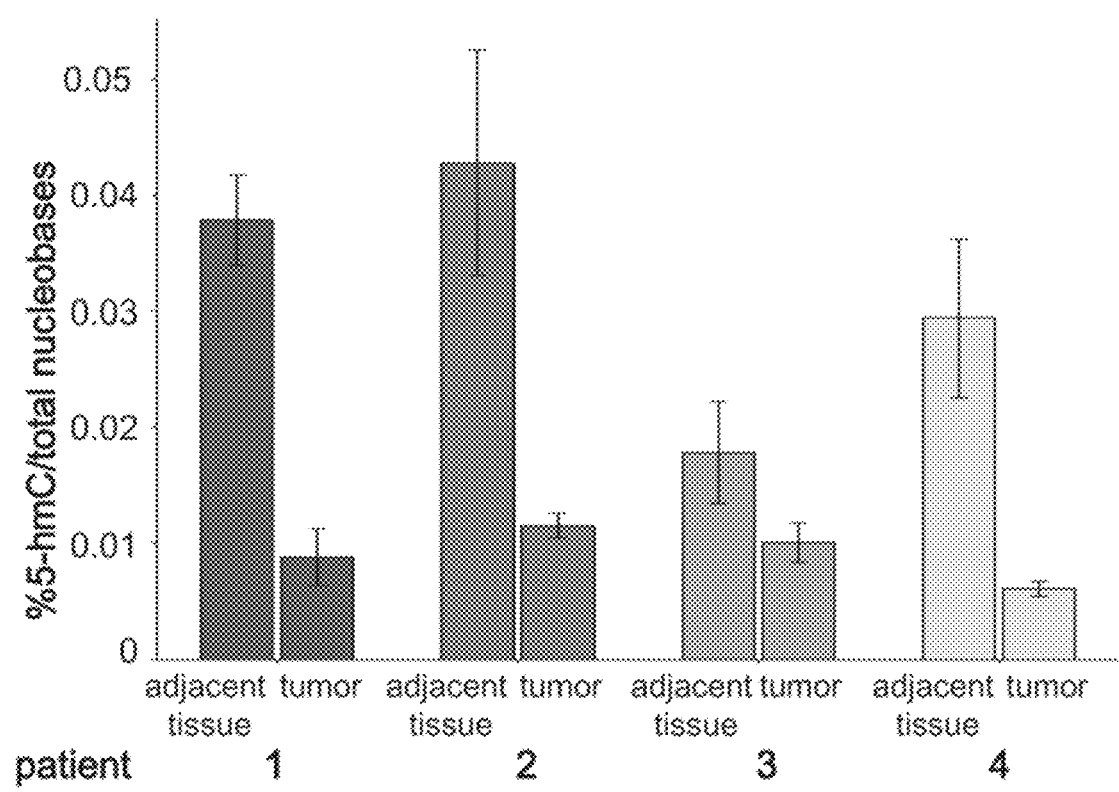
FIGS. 6A and 6B present bar graphs showing 5-hmC levels in pairs of pancreatic tumor and adjacent tissue from 4 pancreatic ductal adenocarcinoma (PDAC) patients (FIG. 6A), and in pairs of colon polyps and adjacent tissue from 2 familial adenomatous polyposis (FAP) patients before and after antibiotic treatment (FIG. 6B) (error bars indicate standard deviations for 4-5 replicates).

As shown in FIG. 6A, the 5-hmC level of the pancreatic tumor was considerably reduced relative to adjacent tissue.

These results indicate that the characteristic reduction in 5-hmC levels occurs also in pancreatic tumors.

Figure 6B:
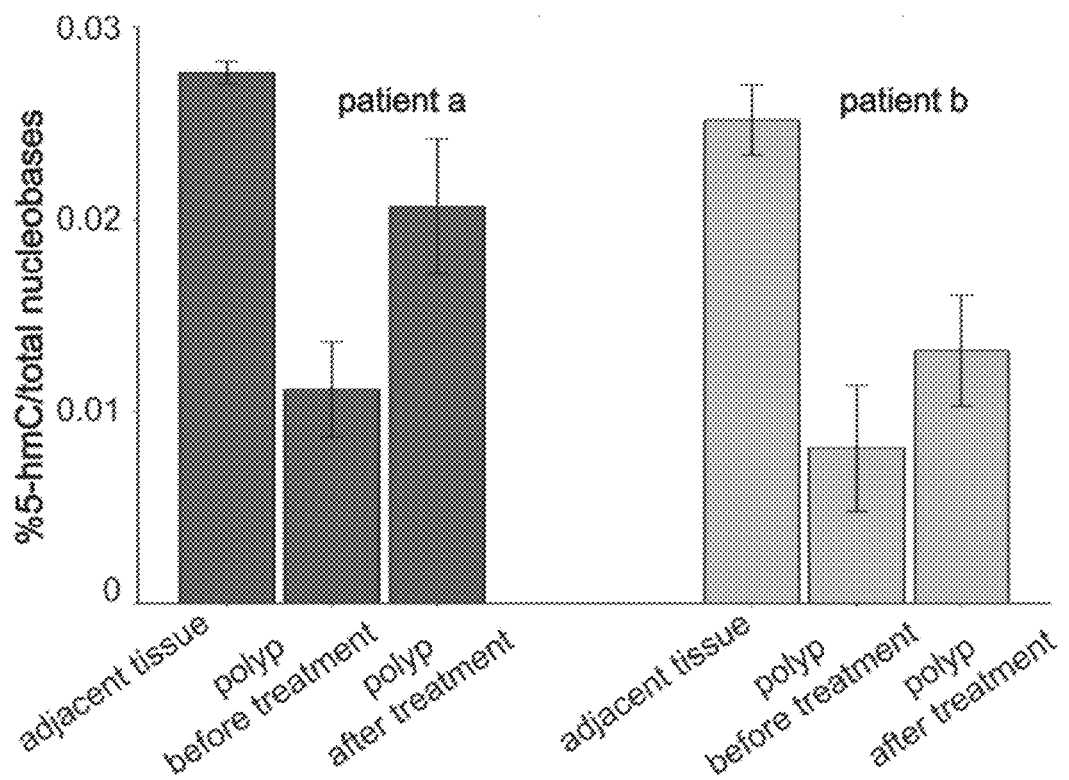

As shown in FIG. 6B, the FAP polyp 5-hmC level after treatment was higher than the polyp 5-hmC level before treatment, and closer to the levels in normal tissue in both patients.

This results indicates that quantification of tissue 5-hmC can be used to distinguish pathological tissue (e.g., polyps) from normal tissue and/or to monitor effects of treatment on pathological tissue (e.g., polyps) and evaluate responsiveness to treatment. For example, 5-hmC quantification as a part of the screening process may provide frequent risk evaluations and an indication for treatment response, which may facilitate decision-making regarding the choice of therapy and patient management based on such measurements.

Figure 7:
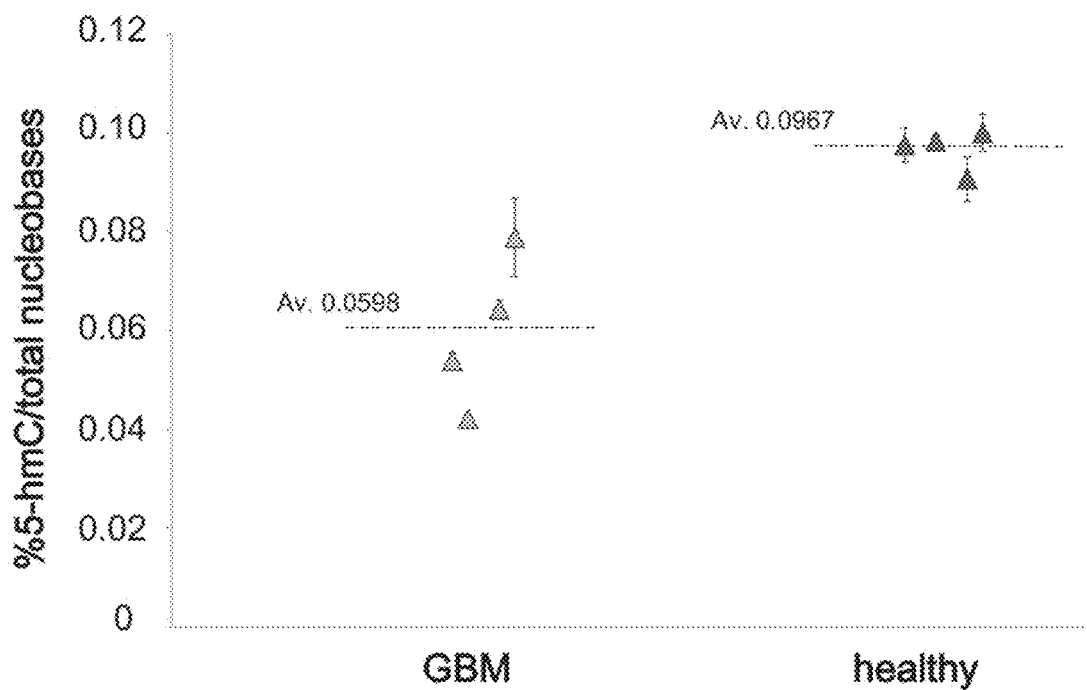
FIG. 7 presents a bar graph showing 5-hmC levels in 4 mouse glioblastoma tumors and 4 normal brain tissue samples from corresponding brain areas (error bars represent standard deviation of 4 replicates)

As shown in FIG. 7, the 5-hmC levels in mouse glioblastoma tumors was significantly lower ($p<0.05$) than in healthy tissue from corresponding areas of mouse brain ($0.05503 \pm 0.01328$ vs. $0.08896 \pm 0.00443$).

These results accord with reports of decreased 5-hmC levels in human glioblastoma [Kraus et al., *Tumour Biol* 2015, 36:8439-8446; Johnson et al., *Nat Commun* 2016, 7:13177; Fernandez et al., *Hum Mol Genet* 2018, 27:3046-3059], and suggest that measurement of 5-hmC levels (according to some embodiments of the invention) in human tumor biopsies can provide additional molecular information about tumor epigenetics, and contribute to the study and profiling of glioblastoma.

Figure 8:
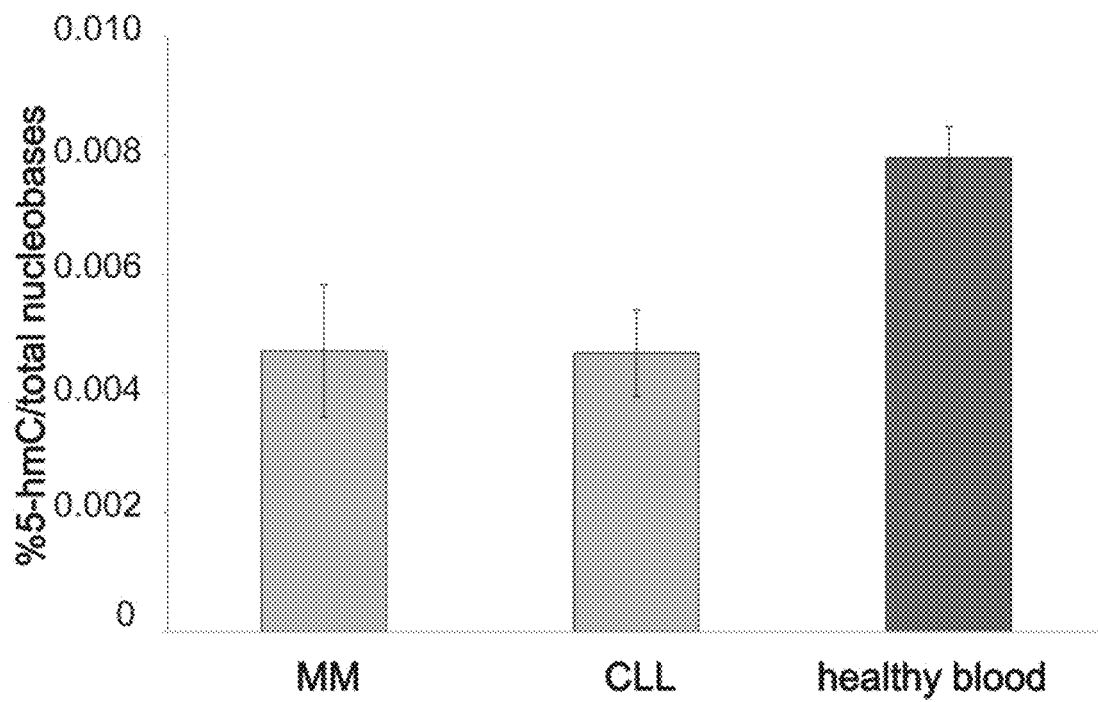
FIG. 8 presents a bar graph showing 5-hmC levels in blood samples from a multiple myeloma (MM) patient, a chronic lymphocytic leukemia (CLL) patient, and a healthy individual (error bars represent standard deviation of 6 replicates).

Similarly, as shown in FIG. 8, the 5-hmC levels in the blood of a multiple myeloma patient (0.0050±0.0010%) and a chronic lymphocytic leukemia patient (0.0047±0.0007%) was about 40% lower than in the blood of a healthy individual (0.0079±0.0005%).

These results confirm that 5-hmC quantification according to some embodiments of the invention is sufficiently sensitive to profile various malignancies.

Example 4

Determination of DNA Damage Associated with UV Radiation

Exposure to UV radiation from the sun is one of the most common sources of DNA damage. UV radiation acts either by promotion of reactive oxygen species (ROS) that oxidize DNA, or by directly inducing formation of cyclobutane pyrimidine dimers (CPDs) or the more potent 6-4 photoproducts. These cross-linked bases can be misinterpreted during transcription and replication to cause mutations and, in severe cases, even complete pausing of replication that induces tension on the replication fork, rendering the DNA, susceptible to double-strand breaks.

DNA damage and repair are linked to fundamental biological processes such as metabolism, disease, and aging. Single strand lesions are the most abundant form of DNA damage; however, reliable methods for characterizing these lesions are lacking.

A multi-sample array prepared as described hereinabove was used to quantify DNA damage associated with UV radiation in a cell line. The assay for the quantification of the DNA damage lesions utilized procedures described by Zirkin et al. [*J Am Chem Soc* 2014, 136:7771-7776]. Briefly, the assay takes advantage of the repair capacity of a bacterial enzymatic cocktail to repair damaged DNA in vitro and incorporate fluorescent nucleotides (labeled with ATTO-647) into damage sites as part of the repair process. The repair enzymes replace a single strand damage site on a double stranded DNA with a fluorophore, so that the obtained fluorescent intensity is proportional to the amount of the DNA damage.

Each DNA damage labeling reaction contained the following: 500 ng purified DNA, 3 μl ThermoPol® buffer (10×) and 0.3 μl×100 NAD$^+$ (×100) (New England BioLabs), 0.5 μl PreCR® Repair Mix enzymatic cocktail that included repair enzymes, DNA polymerase and DNA ligase, topped to 30 μl total reaction volume with ultrapure water. The samples were incubated for 15 minutes at 37° C. Deoxynucleotides (A,G and C) were then added along with UTP conjugated to the fluorescent dye ATTO-647 to a final concentration of 160 nM, and the sample was heated to 65° C. for two minutes and incubated at 65° C. for additional 15-20 minutes. The sample was allowed to cool to room temperature and then maintained at 4° C. until analyzed. This labeling procedure provides sufficient material for several hundred slides and may optionally be scaled down.

Figure 9A:
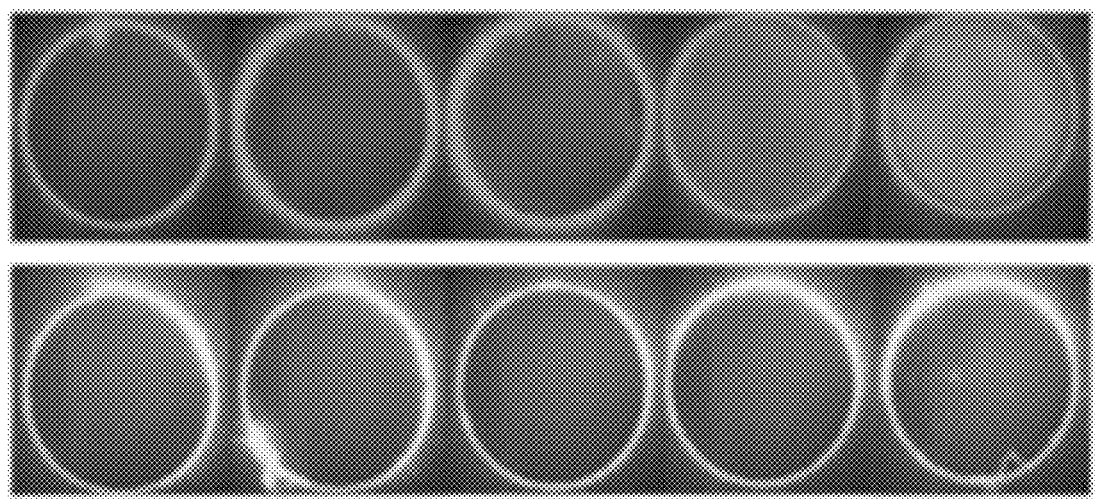
FIGS. 9A and 9B present fluorescence microscopy images (FIG. 9A) of 5 wells in a multi-well array according to some embodiments of the invention containing increasing amounts (0-20 ng) of DNA extracted from irradiated cells treated (upper panel) or not treated (lower panel) with a repair enzyme mix, and labeled with ATTO-647 dye for single strand DNA damage on a double stranded DNA (by utilizing the repair enzymes to replace DNA lesions with a fluorophore); and a graph (FIG. 9B) showing the normalized fluorescent signal of wells such as shown in FIG. 9A as a function of amount of DNA (gray represents DNA treated with repair enzyme mix and black represents DNA not treated with repair enzyme mix; each point represents average of four wells on a single slide).
Figure 9B:
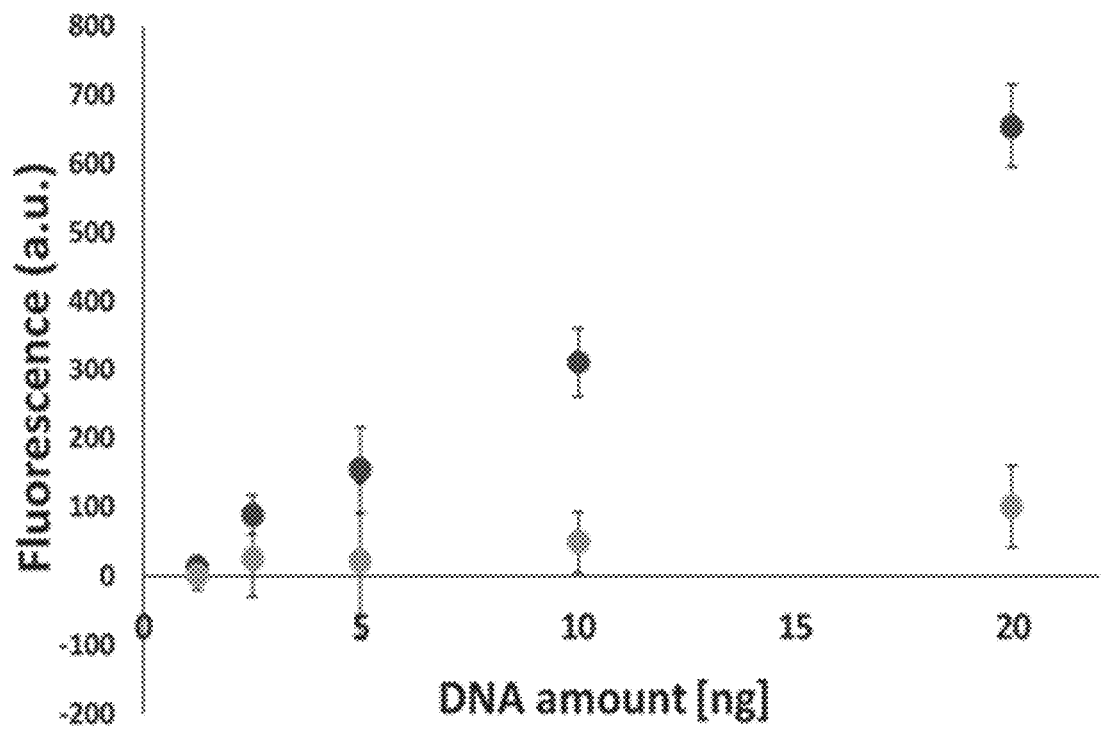

As shown in FIGS. 9A and 9B, a concentration-dependent signal was detected, which was considerably stronger in the tested irradiated DNA than in control DNA (irradiated, but without exposure to repair enzymes).

These results indicate that multi-sample arrays described herein can be used to quantify different types of labeled DNA, including, but not limited to, labeled single strand DNA damage and labeled 5-hmC.

The ability of an exemplary assay to quantify repair dynamics in vivo was then assessed. DNA was extracted from mice at several time points after the mice were subjected to UVB radiation. The DNA was then labeled using T4 PDG (pyrimidine dimer glycosylase), using procedures similar to those described hereinabove for the PreCR® Repair Mix cocktail, except that T4 PDG and endonuclease IV were used instead of PreCR® Repair Mix cocktail. The labeled samples were deposited into wells of an activated glass slide which was imaged and analyzed (according to procedures described hereinabove).

Figure 10:
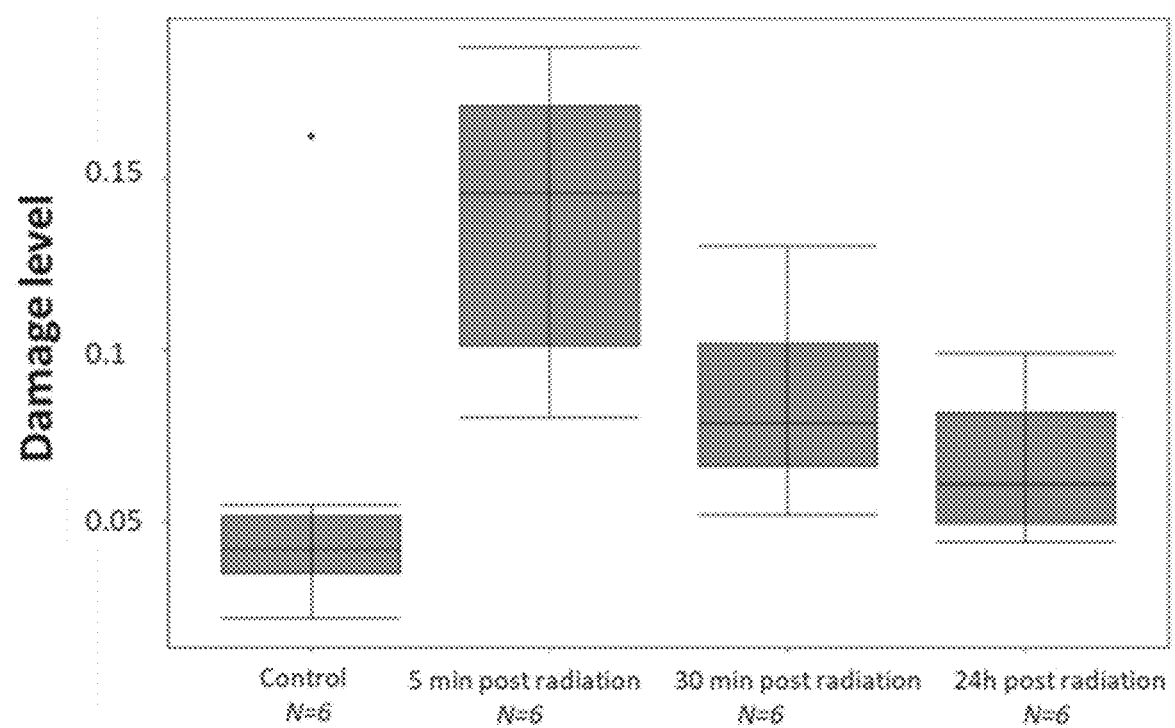
FIG. 10 presents a boxplot representation showing the level (including average and distribution) of DNA damage in DNA extracted from mice subjected to UVB radiation, at 5 minutes, 30 minutes or 24 hours after radiation (non-irradiated mice served as control), as determined by fluorescent labeling of DNA damage using T4 PDG (pyrimidine dimer glycosylase) according to some embodiments of the invention.

As shown in FIG. 10, the damage signal was highest shortly after irradiation of the mice, and declined gradually thereafter.

These results indicate that assays described herein can monitor the repair of DNA over time.

In addition, the use of exemplary assays to quantify different types of DNA modification simultaneously was assessed.

U2OS cells were irradiated with UVB light (302 nm) for 1, 3 or 5 minutes (control cells were not irradiated). After radiation, the cells were harvested and DNA was extracted. For each time point, DNA was labeled in two colors: repair of UV damage was specifically labeled with ATTO-647 (red) using T4 PDG (according to procedures such as described hereinabove), and 5-hmC was specifically labeled with TAMRA (green) using a two-step procedure such as described hereinabove.

Figure 11A:
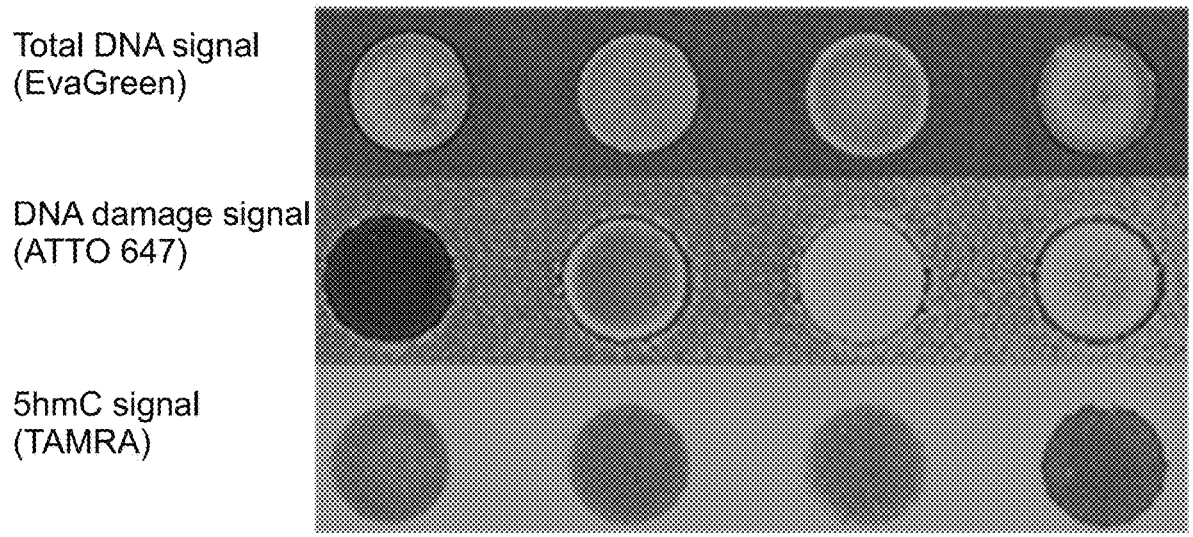
FIGS. 11A and 11B present fluorescence microscopy images (FIG. 11A) of 4 wells containing DNA extracted from U2OS cells subjected to increasing UVB radiation doses, and labeled with ATTO-647 dye for DNA damage (using T4 PDG), with TAMRA dye for 5-hmC, and with EvaGreen® dye for total DNA; and a graph (FIG. 11B) showing the normalized fluorescent signal of wells such as shown in FIG. 11A as a function of UV dose (each point represents average of 5 wells on a single slide).
Figure 11B:
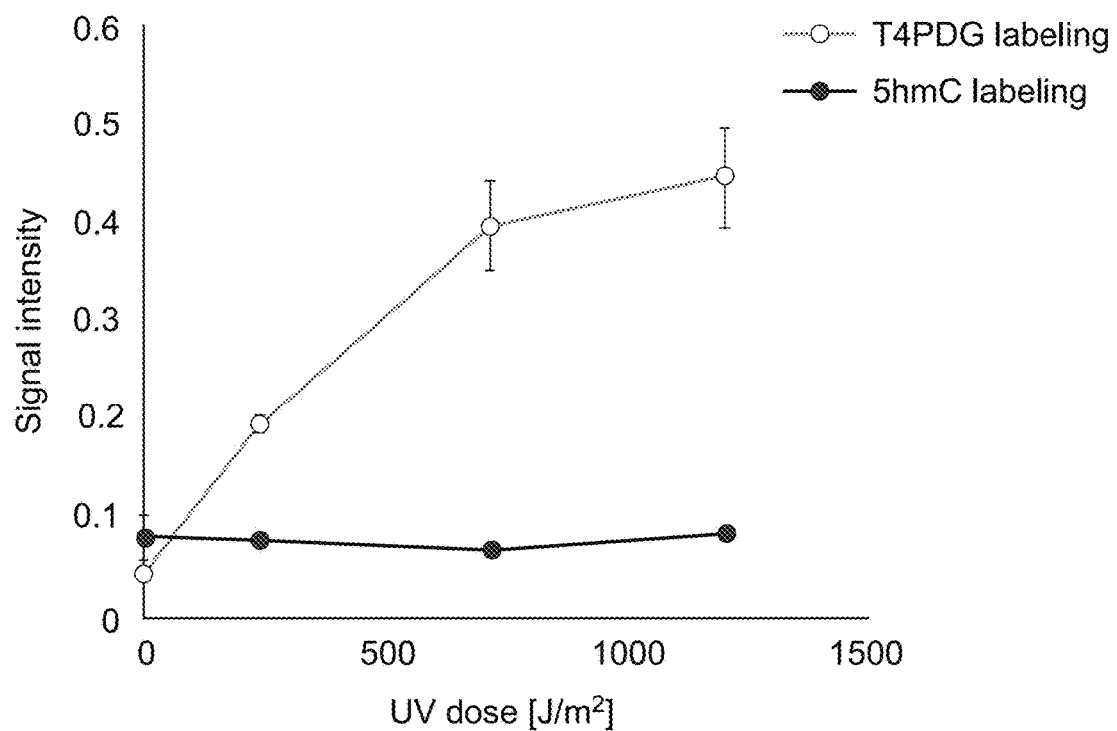

As shown in FIGS. 11A and 11B, the observed DNA damage signal was correlated to UV radiation dose, whereas the simultaneously measured 5-hmC signal was not correlated to the UV radiation dose.

These results indicate that assays described herein can be used to quantify different types of DNA modification simultaneously.

Example 5

Determination of DNA Damage Associated with Oxidation

U2OS cells were treated with various amounts of the oxidizing agent $KBrO_3$ (0-100 mM). After treatment, the cells were harvested and DNA was extracted. The DNA was then labeled with ATTO-550 dye using human 8-oxoguanine glycolase (hOGG1), an enzyme specific for repair of oxidative DNA damage, using procedures similar to those described hereinabove for the PreCR® Repair Mix cocktail, except that hOGG1 and endonuclease IV were used instead of PreCR® Repair Mix cocktail.

Figure 12:
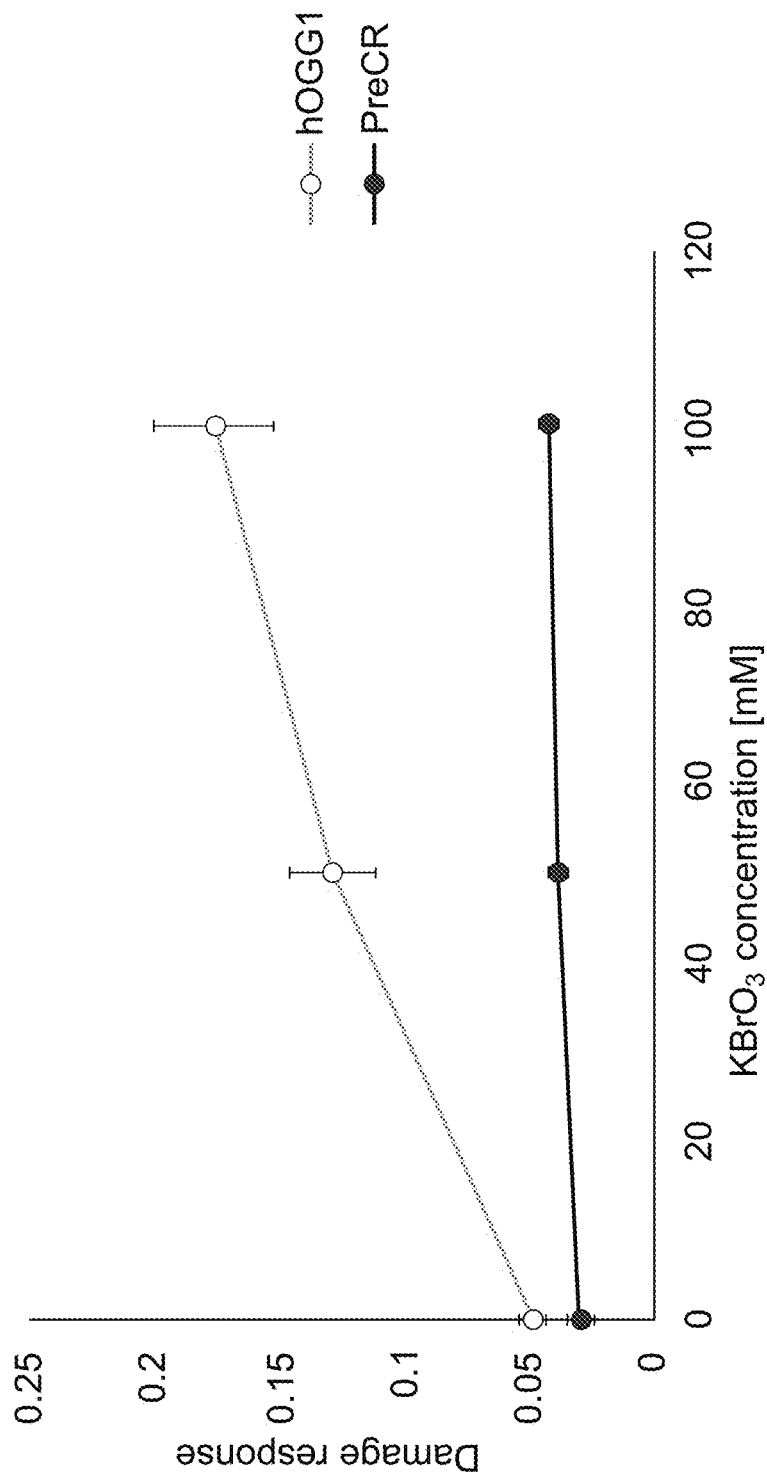
FIG. 12 presents a graph showing levels of DNA damage in DNA extracted from U2OS cells subjected to 0, 50 or 100 mM $KBrO_3$, as determined by fluorescent labeling of DNA damage with ATTO-550 dye using human 8-oxoguanine glycolase (hOGG1) or a repair enzyme cocktail (PreCR® Repair Mix), according to some embodiments of the invention

As shown in FIG. 12, the DNA damage signal was positively correlated with $KBrO_3$ concentration, indicating the sensitivity of the assay utilizing hOGG1 to DNA oxidative damage.

As further shown in FIG. 12, the $KBrO_3$-induced DNA damage was labeled considerably more effectively in the presence of hOGG1 than in the presence of PreCR® Repair Mix.

In order to measure repair dynamics of U2OS cells in situ, cells were treated with 50 mM $KBrO_3$ for one hour, and DNA was extracted from the cells at various time points, ranging from 0 to 24 hours after treatment. DNA samples from the various time points were labeled side-by-side using hOGG1, then deposited into wells of an activated glass slide, which was imaged and analyzed (according to procedures described hereinabove).

Figure 13A:
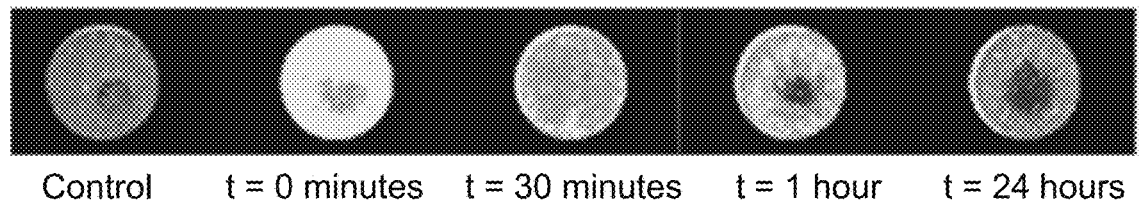
FIGS. 13A and 13B present fluorescence microscopy images (FIG. 13A) of 5 wells containing DNA extracted from U2OS cells 0 minutes, 30, minutes, 1 hour or 24 hours after treatment with 50 mM $KBrO_3$ for one hour, or from untreated control cells, and fluorescently labeled for DNA damage with ATTO-550 using hOGG1; and a bar graph (FIG. 13B) showing the DNA damage (as determined by fluorescent intensity) of wells such as shown in FIG. 13A (each bar represents average of two samples loaded on two separate slides, 5 wells on each slide).
Figure 13B:
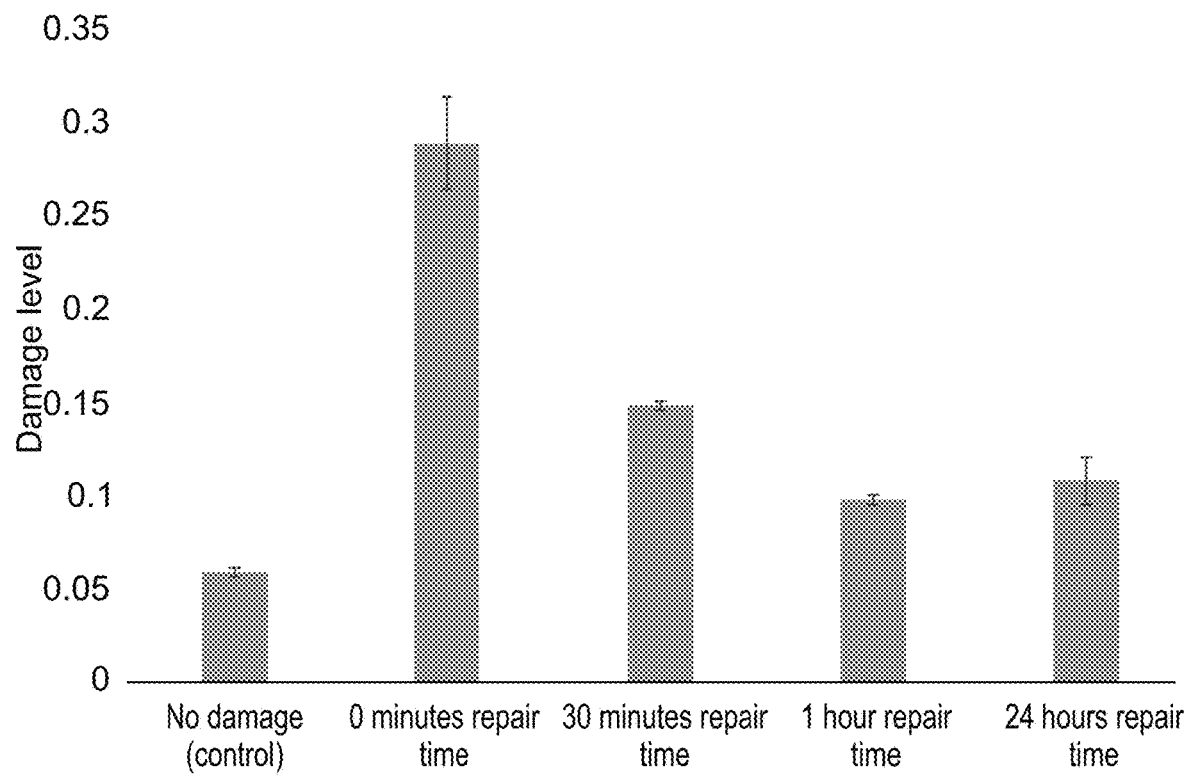

As shown in FIGS. 13A and 13B, the damage signal was highest immediately after treatment, and declined gradually thereafter.

These results indicate that assays described herein can monitor the repair of DNA over time for a variety of types of DNA damage.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method of detecting at least one epigenetic DNA modification in a DNA sample extracted from cells or tissue, the method comprising:
   (a) contacting said DNA of said sample with at least one labeling agent selective for said at least one epigenetic DNA modification, thereby obtaining DNA labeled with said at least one labeling agent, representing said at least one epigenetic DNA modification;
   (b) contacting an aqueous solution comprising said DNA with at least one addressable region on a surface of a substrate, wherein said at least one addressable region comprises a positively charged substance capable of attaching DNA to said surface by electrostatic forces, and said addressable region is surrounded by a hydrophobic region of said surface; and
   (c) determining an amount of said at least one labeling agent in said addressable region, thereby detecting the amount of the at least one epigenetic DNA modification in the DNA sample.

2. The method of claim 1, wherein said at least one labeling agent is an at least one fluorescent labeling agent, and determining said amount of said at least one labeling agent is effected by detecting fluorescence of said at least one labeling agent.

3. The method of claim 1, further comprising washing said surface of said substrate thereby removing said labeling agent which is not bound to said DNA subsequently to attaching said DNA molecule to said surface, and prior to said determining said amount of said DNA labeled with said at least one labeling agent.

4. The method of claim 1, wherein an amount of said DNA in said aqueous solution contacted with said addressable region is in a range of from 5 ng to 300 ng.

5. The method of claim 1, wherein a concentration of DNA in said aqueous solution is in a range of from 5 ng/$\mu$l to 300 ng/$\mu$l.

6. The method of claim 1, wherein a ratio of an amount of DNA in said aqueous solution contacted with said addressable region to an area of said addressable region is in a range of from 1 ng/mm$^2$ to 150 ng/mm$^2$.

7. The method of claim 1, wherein an area of said addressable region is in a range of from 1 mm$^2$ to 10 mm$^2$.

8. The method of claim 1, comprising contacting a plurality of addressable regions with an aqueous solution comprising a plurality of said DNA, wherein said addressable regions separated from each other by a space of at least 1 mm, or of from about 1 mm to about 10 mm or from about 1 mm to about 5 mm, and determining an amount of a plurality of said at least one labeling agent in each of a plurality of addressable regions.

9. The method of claim 1, wherein said positively charged substance comprises polylysine.

10. The method of claim 1, wherein said epigenetic DNA modification is selected from the group consisting of a 5-methylcytosine residue, a 5-hydroxymethylcytosine residue, and DNA damage.

11. The method of claim 1, comprising attaching a plurality of first labeling agents to a DNA molecule, each of said plurality of first labeling agents being selective for a different type of epigenetic DNA modification, and determining an amount of each of said plurality of first labeling agents, thereby detecting a plurality of epigenetic DNA modifications.

12. The method of claim 1, further comprising determining an amount of DNA in said addressable region.

13. The method of claim 12, wherein said determining an amount of DNA is effected by contacting said DNA with a second labeling agent, wherein said second labeling agent binds to DNA.

* * * * *